(12) United States Patent
Chin et al.

(10) Patent No.: US 11,923,051 B2
(45) Date of Patent: Mar. 5, 2024

(54) SYSTEM AND METHOD FOR CREATING DIGITAL THERAPEUTICS DIRECTED TO PATIENT CARE SPECIFIC TO A DISEASE

(71) Applicant: Apricity Health LLC, Houston, TX (US)

(72) Inventors: Lynda Chin, Houston, TX (US); Peter Bahrs, Georgetown, TX (US); Raphael Chancey, Leander, TX (US); Richard Lyle, Leander, TX (US)

(73) Assignee: Apricity Health LLC, Houston, TX (US)

( * ) Notice: Subject to any disclaimer, the term of this patent is extended or adjusted under 35 U.S.C. 154(b) by 393 days.

(21) Appl. No.: 16/690,509

(22) Filed: Nov. 21, 2019

(65) Prior Publication Data
US 2021/0057057 A1 Feb. 25, 2021

Related U.S. Application Data

(60) Provisional application No. 62/888,777, filed on Aug. 19, 2019.

(51) Int. Cl.
*G16H 10/60* (2018.01)
*G06F 40/30* (2020.01)
(Continued)

(52) U.S. Cl.
CPC ............ *G16H 10/60* (2018.01); *G06F 40/30* (2020.01); *G06N 5/02* (2013.01); *G06N 20/00* (2019.01);
(Continued)

(58) Field of Classification Search
None
See application file for complete search history.

(56) References Cited

U.S. PATENT DOCUMENTS

| 2009/0187425 A1* | 7/2009 | Thompson .............. G10L 15/26 705/3 |
| 2019/0130073 A1* | 5/2019 | Sun .................... G06K 9/00442 |
| 2019/0251169 A1* | 8/2019 | Loghmani ............... G06F 40/30 |

FOREIGN PATENT DOCUMENTS

WO WO-2019074545 A1 * 4/2019 ........... A61B 5/7267

OTHER PUBLICATIONS

Hatzivassiloglou, Vasileios. "Automatic Acquisition of Lexical Semantic Knowledge from Large Corpora: The Identification of Semantically Related Words, Markedness, Polarity, and Antonymy." Order No. 9910594 Columbia University, 1998. Ann Arbor: ProQuest. Web. Oct. 6, 2023. (Year: 1998).*

* cited by examiner

*Primary Examiner* — Lena Najarian
(74) *Attorney, Agent, or Firm* — Terrile, Cannatti & Chambers, LLP; Emmanuel A. Rivera

(57) ABSTRACT

A system, method, and computer-readable medium are disclosed for digital therapeutics directed to patient care specific to a disease. Digital therapeutics (DTx) knowledge models are created and their corpus is validated. Condition and symptom models are created for processing the digital therapeutics (DTx) knowledge models. Clinical and condition models are converted to reconfigurable runtime implementations. Architecture and implementation subsets of knowledge models, language models, condition and symptom models, technology and tools are created. Digital therapeutics (DTx) natural language models are created. Multiple program content versions of natural language content, clinical physician, and condition models are created.

30 Claims, 20 Drawing Sheets

(51) Int. Cl.
*G06N 5/02* (2023.01)
*G06N 20/00* (2019.01)
*G16H 10/20* (2018.01)
*G16H 10/40* (2018.01)
*G16H 20/00* (2018.01)
*G16H 30/20* (2018.01)
*G16H 50/20* (2018.01)
*G16H 50/50* (2018.01)
*G16H 50/70* (2018.01)
*G16H 70/20* (2018.01)
*G16H 70/40* (2018.01)

(52) U.S. Cl.
CPC ............. *G16H 10/20* (2018.01); *G16H 10/40* (2018.01); *G16H 20/00* (2018.01); *G16H 30/20* (2018.01); *G16H 50/20* (2018.01); *G16H 50/50* (2018.01); *G16H 50/70* (2018.01); *G16H 70/20* (2018.01); *G16H 70/40* (2018.01)

| Home | Alerts | Missed Check-ins | Follow-ups | Reference | ✱ | ⚙ | Patient search |

1300 ⟶

Collapse all     Filter: Unverified

Red Alerts

| Name | Age | Gender | Chief Complaint | Date and time of report | Score | Verified | Patient Status |
|---|---|---|---|---|---|---|---|
| Comp19L forward212 | 46 | Male | Fatigue, Shortness of breath | 4/11/2019, 11:54 AM | 18.5 | ⊙ | Verification and Evaluation needed |
| Blue643 Mobeller | 42 | Male | Diarrhea, Headache, muscle weakness | 4/11/2019, 7:47 AM | 26.5 | ⊙ | Verification and Evaluation needed |
| Alux444 Aussin000 | 42 | Female | Cough, Shortness of breath, Rash | 4/11/2019, 7:46 AM | 10.6 | ⊙ | Verification and Evaluation needed |
| Alaska777 Ano000 | 47 | Female | Difficulty swallowing complain Eye pain or vision change, Diarrhea | 4/11/2019, 7:42 AM | 10.7 | ⊙ | Verification and Evaluation needed |

Yellow Alerts

| Name | Age | Gender | Chief Complaint | Date and time of report | Score | Verified | Patient Status |
|---|---|---|---|---|---|---|---|
| Burner49 Blade20 | 19 | Male | Rush, Diarrhea, Fatigue and muscle | 4/11/2019, 10:10 AM | 20.6 | ⊙ | Verification and Evaluation needed |
| Fiction876 Pulo838 | 20 | Male | Fatigue, Muscle weakness | 4/11/2019, 7:39 AM | 3.9 | ⊙ | Verification and Evaluation needed |
| Lyle787 Richan667 | 49 | Male | Rash | 4/11/2019, 7:42 AM | 6.5 | ⊙ | Verification and Evaluation needed |
| Patient synthetic | 8 | Female | Rash, Diarrhea | 4/11/2019, 11:12 AM | 14.1 | ⊙ | Verification and Evaluation needed |

Green Alerts

No Portion

| Home | Clinical profile | Summary | Triage Wokup | Treatment | Guidelines | ✱ | ✿ | Patient search 🔍 |

Juno00 Alaska77 Patient No. 6b9da7ca7efa DOB: 2/1/1972 Age: 47 Gender: Female Phone: +1 999-999-9999 Patient Status: Verification and Evaluation Needed ( 10.7 ) | Diagnosis ⌄ | Current IO Treatment ⌄ | Prior irAE / Pre-existing AID ⌄ | Allergies ⌄ |

Recommendations for: Combined Difficulty swallowing   Eye pain or vision change (grade 2), R/O Uveities   ASCO   ⊕ Add   ☐ Print
complaint (grade 4), R/O mystics                                                                    guidelines    notes    screen
Diarrhea (grade 1), R/O colitis

| Clinical Pearls |

Lab Tests
☑ CBC with diff. & cvp
☑ CK & impound
☑ CSR & CSP
☑ LCM & alcoholic
☑ Computer ************

Consults
☑ Urgent neurology consult
☑ Urgent ******* consult

Place of care
☑ **********
☑ CK & impound

Physical Exam
☑ Computer ************
☑ ******************************

| Home | Clinical profile | Summary | Triage | Wokup | Treatment | Guidelines | & | 🕮 | Patient search | 🔍 |

Juno00 Alaska77 Patient No. 6b9da7ca7efa DOB: 2/1/1972 Age: 47 Gender: Female Phone: +1 999-999-9999   Patient Status:
Verification and Evaluation Needed (10.7)   Diagnosis ⌄    Current IO Treatment ⌄    Prior irAE I Pre-existing AID ⌄    Allergies ⌄

Recommendations for: Combined  Difficulty swallowing  Eye pain or vision change (grade 2), R/O Uveities  ASCO  ⊕ Add  ◻ Print
complaint (grade 4), R/O mystics                                                                 guidelines   notes   screen
Diarrhea (grade 1), R/O colitis Clinical Pearls Lab Tests
☑ **********                    Place of care
                                ☑ **********
Consults
☑ **********                    Physical Exams
                                ☑ **********
Procedure
☑ **********                    IO Therapy
                                ☑ **********

SYSTEM AND METHOD FOR CREATING DIGITAL THERAPEUTICS DIRECTED TO PATIENT CARE SPECIFIC TO A DISEASE

RELATED APPLICATIONS

This application claims the benefit of priority of U.S. Provisional Patent Application Ser. No. 62/888,777, filed Aug. 19, 2019, incorporated herein by reference.

BACKGROUND OF THE INVENTION

Field of the Invention

The present invention relates to information handling systems. More specifically, embodiments of the invention relate to artificial intelligence systems for digital therapeutics directed to patient care specific to a disease.

Description of the Related Art

In treating patients with cancers or serious diseases, several approaches can be taken, including radiation, chemical, surgical, and immunotherapy. Immunotherapy makes use of a body's natural defenses or immune system to fight disease. An area of immunotherapy used to specifically treat cancer is known as immuno-oncology (TO). Cancerous cells can thrive because of their ability to hide from immune systems. Immunotherapies or IO can mark cancer cells to allow immune systems to find and destroy cancer cells. Certain immunotherapies or IO can boost immune systems to better fight against cancer.

Part of IO therapy or treatment includes activating a body's immune system response to overcome cancerous tumor survival and growth. The treatment can also cause adverse side effects, such as attacks on healthy cells while attacking cancerous cells. Such adverse responses can be referred to as Immune-mediated or Immune Related Adverse Event or irAE. irAE can affect any organ system in the body, including the gastrointestinal tract, skin, heart and lung, liver and kidneys, the nervous system or brain, endocrine organs such as thyroid, pancreas, and many others. Examples of irAE symptoms can include joint pain, swelling, soreness, redness, skin itchiness, rashes, fever, chills, dizziness, nausea, vomiting, muscle/joint paint, fatigue, headaches, trouble breathing, low/high blood pressure, swelling, retaining fluid, heart palpitations, sinus congestion, diarrhea, infection, vision problem etc.

Ongoing irAEs can lead to complications or end of life. It is understandable, that individual patients will have different reactions to certain immunotherapies or IO based on age, gender, genetics, prior medical history, cancer type, mutation type, and other differentiators. It is also understandable the categorically similar patients, once appropriately defined, may have categorically similar reactions to certain immunotherapies or IO. Patient's irAEs will be different and can dynamically change over time. Effective management of treatment of patients, assuring that better good is done than harm, is to accurately understand the therapy and effects of such therapy for each individual patient.

SUMMARY OF THE INVENTION

A system, method, and computer-readable medium are disclosed for digital therapeutics directed to patient care specific to a disease. Digital therapeutics (DTx) knowledge models are created and their corpus is validated. Condition and symptom models are created for processing the digital therapeutics (DTx) knowledge models. Clinical and condition models are converted to reconfigurable runtime implementations. Architecture and implementation subsets of knowledge models, language models, condition and symptom models, technology and tools are created. Digital therapeutics (DTx) natural language models are created. Multiple program content versions of natural language content, clinical physician, and condition models are created.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

FIG. 13 shows a screen presentation of a health care provider user interface;

FIG. 14 shows a screen presentation of a health care provider user interface;

FIG. 15 shows a screen presentation of a health care provider user interface;

FIG. 16 shows a screen presentation of a health care provider user interface;

FIG. 17 shows a screen presentation of a health care provider user interface;

FIG. 18 shows a screen presentation of a health care provider user interface;

FIG. 19 shows a screen presentation of an authoring tool user interface;

FIG. 20 shows a screen presentation of an authoring tool user interface;

DETAILED DESCRIPTION

Figure 1:
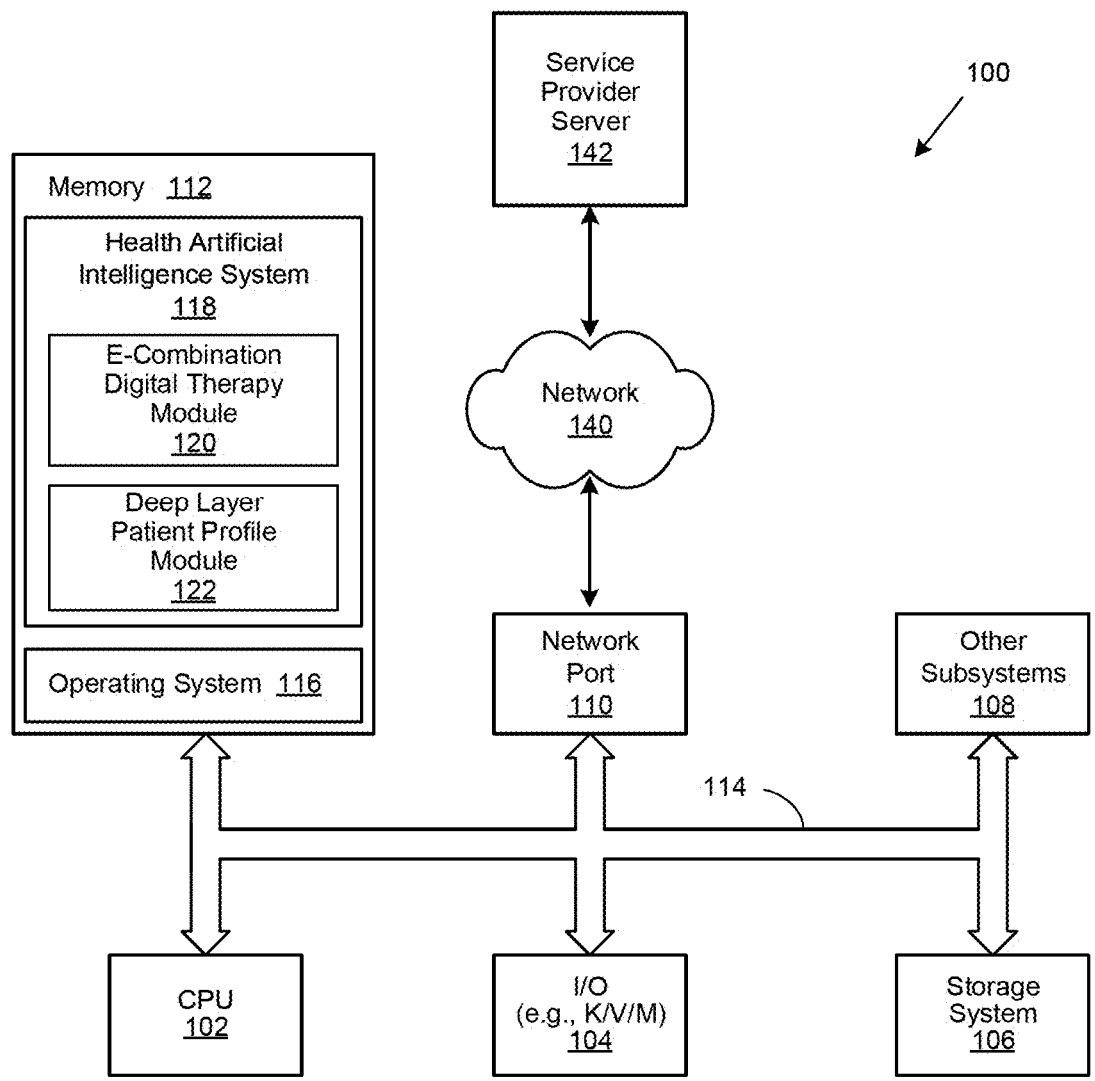
FIG. 1 shows a general illustration of components of an information handling system as implemented in the system and method of the present invention.

Digital Therapeutics (DTx) includes software programs that provide efficacious interventions to patients to prevent, manage, or treat a broad spectrum of physical, mental, and behavioral conditions. DTx can capture scientific evidence and expert knowledge about a cancer type and its treatment with a specific drug or class of drugs. DTx captures and integrates real time patient data and clinical information. DTx can generate insights personalized to a specific patient. When prescribed together with an anti-cancer drug, DTX can incorporate real-time patient data in context of curated clinical knowledge to generate personalized insights in clinically relevant time, activating the appropriate healthcare providers at the right time to detect, diagnose and treat irAEs. This concept is expressed simply as DTx+drug therapy=precision and personalization.

As cancer patients are treated with immunotherapy, such as immuno-oncology (TO), positive effects towards treating the disease are expected; however, in certain instances during treatment, adverse effects from the treatment can be experienced. If the adverse effects continue, the patient can experience severe complications. Furthermore, if a costly drug treatment or clinical drug trial is involved and adverse effects are not properly identified, the investment may be compromised. Determining such adverse effects and their causes can be performed using intelligent information handling systems that gather and store information, such as patient symptoms during treatment.

An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is protected, how the information is handled, how much information is processed, stored, or communicated, and how quickly and efficiently the information may be processed, stored, or communicated. In addition, information handling systems may include a variety of hardware and software components that may be configured to process, store, and communicate information and may include one or more computer systems, data storage systems, and networking systems.

For purposes of this disclosure, an information handling system may include any instrumentality or aggregate of instrumentalities operable to compute, classify, predict, protect, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, a camera, a microphone, and a video display. The information handling system may also include one or more buses operable to transmit communications between the various hardware components.

FIG. 1 is a generalized illustration of an information handling system 100 that can be used to implement the system and method of the present invention. The information handling system 100 includes a processor (e.g., central processor unit or "CPU") 102, input/output (I/O) devices 104, such as a display, a keyboard, a mouse, and associated controllers, a hard drive or disk storage 106, and various other subsystems 108. In various embodiments, the information handling system 100 also includes network port 110 operable to connect to a network 140, which is likewise accessible by a service provider server 142. The information handling system 100 likewise includes system memory 112, which is interconnected to the foregoing via one or more buses 114. System memory 112 further comprises operating system (OS) 116 and in various embodiments may also comprise a health artificial intelligence or AI system 118.

In certain embodiments, the health AI system 118 includes multi-treatment digital therapy module 120 and deep layer patient profile (DLPP) module 122. The deep layer patient profile (DLPP) module 122 can store longitudinal data as a deep layer patient profile (DLPP). The health AI system 118 can provide digital therapeutics or DTx on medical patients, delivering evidence-based therapeutics, which can be intervention of pending/planned treatment, to prevent, manage, or treat a medical disorder or disease, and in this example cancer. DTx delivers evidence-based therapeutic interventions to patients using software programs to prevent, manage, or treat a medical disorder or disease. DTx are used independently or in together with medications, devices, or other therapies to optimize patient care and health outcomes. DTx can be independently implemented, or can be used with medication, medical devices, and other therapies to optimize patient care and treatment results.

DTx is implemented to provide detection, evaluation, treatment, and management of treatment related adverse events. Outcomes are specific to patients and can have variable outcomes. In certain implementations, various technics can be used including genomic sequencing of blood, tissue, or stool, blood or urine maker determination, for detection, evaluation and treatment, etc. In certain implementations, phenomics data collected from patients, measured with connected devices, via mobile phone, web, or other connected means, in addition to clinical data from electronic health records (EHR), can be used to develop predictive models to guide precision management. An integrated digital care pathway can be provided, that is informed by data and evidence, for management of treatment-related adverse events or Immune Related Adverse Events (irAE). Scientific and expert evidence is captured about a disease and treatment with specific drug(s). In addition, real-time patient data and clinical information is captured and integrated. Personalized/specific insight is generated for specific patients.

Figure 2:
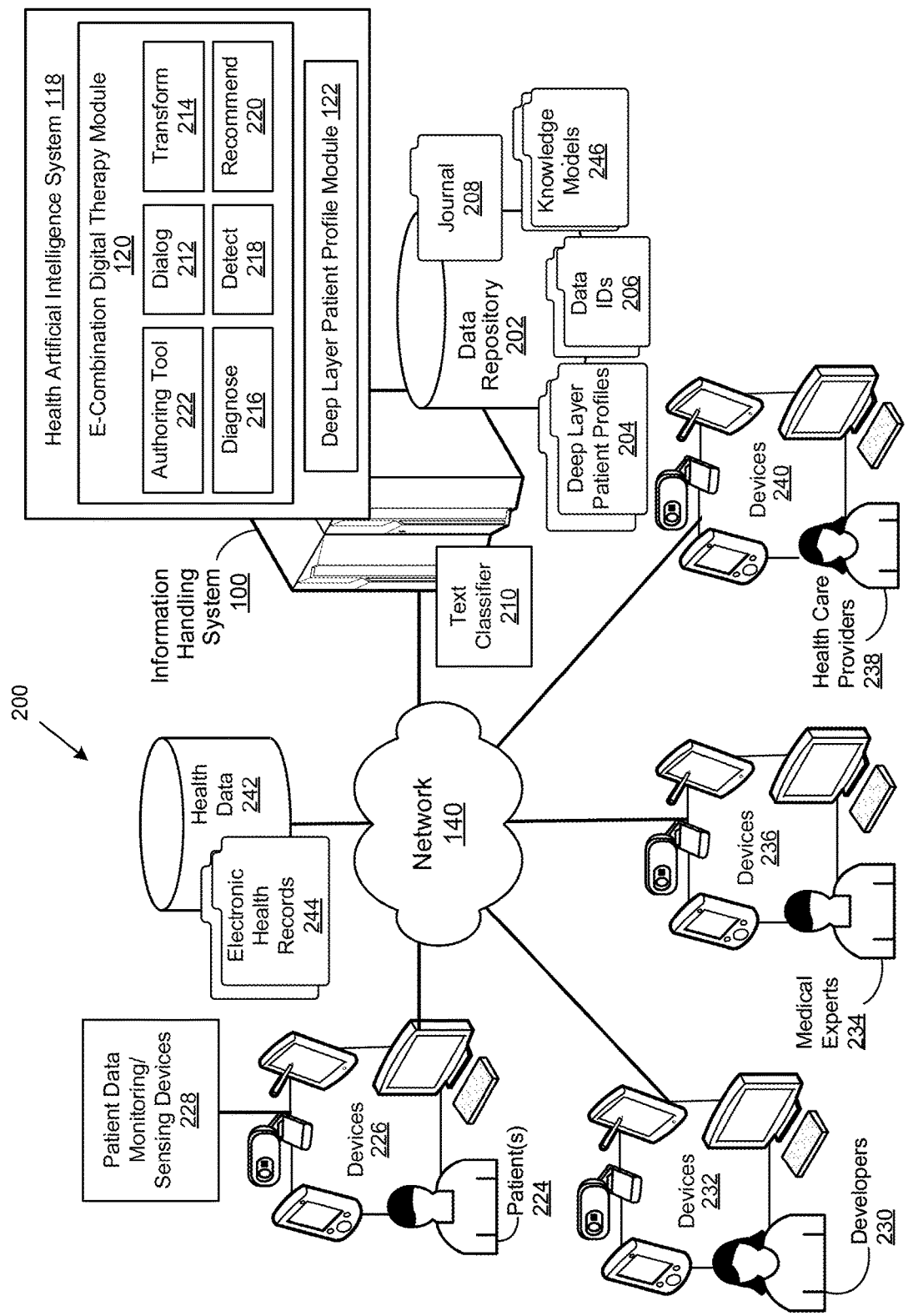
FIG. 2 shows a block diagram of a health AI environment.

FIG. 2 is a block diagram of a health artificial intelligence (AI) environment 200 implemented in accordance with an embodiment of the invention. The health AI environment 200 includes the information handling system 100 which includes the health AI system 118. The health AI system 118 includes the E-combination digital therapy module 120 and deep layer patient profile (DLPP) module 122. In certain implementations, the information handling system 100 includes a data repository 202 which can store information, such as patient data processed by the information handling system 100. In certain implementations, the data repository 202 can be configured to store patient related data, such as deep layer patient profiles (DLPP) 204 and data identifiers (IDs) 206. The deep layer patient profile (DLPP) module 122 can be used to generate deep later patient profiles (DLPP) 204. Deep layer patient profiles (DLPP) 204 can be continuously updated as further described below. Deep layer patient profiles (DLPP) 204 can include patient identifier (ID), recommendations, patient data entered through the health AI environment 200, electronic health records (EHR) electronic medical records (EMR), etc. In certain implementations, context entered through the health AI environment 200 includes deep layer patient profiles (DLPP) 204, where context can be a session with a deep layer patient profile (DLPP) with questions answered, and type of data that is desired, such as time zone, language, required or optional data, longitudinal data (e.g., over 14 day time period), etc.

Data IDs 206 can be used to identify data. For example, data is collected as to DTx knowledge models and symptoms as further described below. In certain implementations, data IDs 206 can be used to identify collected data, such as gathered answers to patient questions. In certain implementations, the data repository 202 includes a journal 208, which for example, can store scores related to symptoms of different categories. In certain implementations, the data repository 202 includes DTx knowledge models 246.

The following code describes example knowledge models:

Priority Inversion: for a selection, after a previous high priority selection is identified and processed, if the current priority selection is the same as previous for N times, reduce the current priority so that the next selection with a lower priority can be processed. Derivatives: for values 0, 1, 2, . . . , N; if 0, then use the current value for any longitudinal selection as is (e.g. blood pressure, or headache); if 1, then take the derivative (i.e., change) of current and previous K values to determine the change in longitudinal items; a positive change (i.e., slope) can indicate an increasing value; if 2, then take the 2nd derivative (i.e., change in slope). Weighted Inversion: divide selection priority by weight. Chaining: when multiple selections are weighted resulting in the same evaluation, a chain identifies a list of selection types that are processed left to right for final arbitration, (e.g., colitis, endocrinopathy, etc.). Environmental: reduce impact of selection weight by D % with accompanying environmental condition is present, (e.g., headache with "sun exposure." Lab: modify impact of selection weight by M % based on lab result. LikeMe: modify weights in DLPP

```
DTx knowledge models categorization
    Domain: Oncology
        Program: Adverse Event Toxicity Management
            Questions - languages and genres
            Rules - pre and post conditionals and groups
            Actions - additional actions - dialog, rules, actions
            Detect Models
                Trigger - Symptom that drives model to be activated (e.g. rash for dermatitis,
diarrhea for colitis)
                Primary Symptom - Priority, Weights, ID (e.g. headache)
                Associated Symptom - Priority, Weights, ID (e.g. location, severity, etc. of
headache)
                Clinical Modifier - Priority, Weights, ID (e.g. had prior irAE)
            Diagnostic Models
                Clinical lab results drive model to be activated (e.g. confirmed rash for
dermatitis)
                Primary Symptom - Priority, Weights, ID (e.g. headache)
                Associated Symptom - Priority, Weights, ID (e.g. location, severity, #)
                Clinical Modifier - Priority, Weights, ID (e.g. had prior irAE)
            Recommendation Models
                Pre-Conditions - Rule / Conditional / Time Trend
                    Recommendation 1 - weight (1 physician required, 0 optional),ID (text)
                    Recommendation ...N
        #expanded Programs
        Program: Chemotherapy
        Program: Radiation therapy
        Program: Immunotherapy
        Program: Surgery
        Program: Targeted therapy
        Program: Hormone therapy
    #expanded Domains
    Domain: Heart Disease, etc.
    Domain: Shared
        Program: Shared
            Medications
            Conditions
            Data types
```

In certain implementations, DTx calculations provide for weight variables to be adjusted based on organization preference, expert opinion or AI/ML algorithms. Weight variables can be applied to, and are not limited to the following types: questions, symptoms, recommendations, rules, conditions, and actions, etc. Weights can be used to emphasize results, remove results, adjust priorities, or affect calculations. Weights can be applied to a category, a list of categories, an item, a list of items, or a chain of any of the aforementioned.

When selecting or applying to a category, the following weight variables and/or operations can be included. Priority: for a selection, multiply the selection's priority by a weight.

based on a function of weights resulting from P other patients or L other lab results; the function( ) can include replaced, multiply, divide or any of the previous weights.

In certain implementations, the information handling system 100 can include a text classifier 208. Data or information can be received in a specific format as defined by a media type, or in certain instances a Multipurpose Internet Mail Extensions or mime type. The text classifier 208 can be used to covert mime types to accessible text or data/information that is stored. In certain implementations, an answer type (e.g., text, speech, image, etc.) will indicate how to store data. Standard text classification can be implemented, such as speech to text, text to speech, image to text, text to image, etc.

In certain embodiments, the health AI system 118, and digital therapy module 120, can include various components. In certain implementations, such components include, a dialog component 212, a transform component 214, a diagnose component 216, a detect component 218, and a recommend component 220. The components will be further discussed below. The digital therapy module 120 can also include an authoring tool 222. The authoring tool 222 can be used by entities, such as medical experts, and implemented to author/provide: questions, answers IDs, priorities, conditions, languages, etc. The authoring tool 222 further can deploy DTx knowledge models.

In certain implantations, multiple domains, programs, diseases, symptoms, subject matter expert knowledge models for the dialog component 212, a transform component 214, a diagnose component 216, a detect component 218, weight, priorities and genres are supported.

The information handling system 118 can connect to network 140. Network 140 is representative of various networks, that include internal and external networks, secure and unsecure networks, various computing devices, such as servers, cloud computing networks and devices, etc. For certain implementations, the described entities of health AI environment 200 are provided limited or secure access to certain networks and computing devices of network 140.

The health AI environment 200 includes patient(s) 224 who are monitored and provided treatment, such as immunotherapy or immuno-oncology (TO). Patient(s) 224 can use patient devices 226 to provide information and to receive information. In certain implementations, patient data monitoring/sensing devices 228 can collect or gather information or data about patient(s) 224. For example, patient data monitoring/sensing devices 228 can include personal wearable devices, heat or optical measurement devices that detect temperature and images of the patient(s) 224. In certain implementations, the patient data monitoring/sensing devices 228 can provide information or data to devices 226 by wireless transmission, such as Bluetooth.

As used herein, a device 226 refers to an information handling system such as a personal computer, a laptop computer, a tablet computer, a personal digital assistant (PDA), a smart phone, a mobile telephone, a camera, a mirror, a robot or other device capable of communicating and processing data. In certain implementations, device 226 can present patient(s) 224 with patient related questions, as part of a conversion or dialog for digital therapeutics. In certain implementations, the conversion or dialog is performed through the dialog component 212. In particular, the dialog component 212 receives patient answers to health symptom dialog questions. The dialog component 212 can further send questions to the patient for additional patient related information. In certain implementations, the patient answers are in response to modified dialog questions from detect and diagnose questions. Modified questions can be the result from reducing conflicting questions, changing questions based on a specific genre question syntax, re-categorized and re-ordered questions based on priority resolution, and additional questions for subjective reduction.

The conversation or dialog from dialog component 212, as to the questions can be performed with devices 226 through various entry points such as applications and web browsers running on the devices 226. Answers to the questions can be obtained by entering text or information directly on devices 226 or can be gathered through specific patient data monitoring/sensing devices 228 such as a smart mirror which can detect facial expressions (e.g., facial image data), a microphone which can detect voice inflections, fixed and moveable robotics, personal cameras, etc. For example, data related to answers can be obtained through artificial intelligence (AI) which can include sentiment analysis (e.g., elated, happy, sad, angry), voice changes (faster, slower, louder, quieter), image changes (facial lines, weight loss, growing rash), etc. Patient answers can be presented through a user interface, audio input and output, camera input and output, and gesture input and output, etc.

The questions from the dialog component 212 can be structured to receive answers from the patient(s) 224 to be used by the information handling system 100 and specifically the E-Combination digital therapy module 120 and its components as described herein. The answers can also be used by other entities of health AI environment 200 as further described below. In certain implementations, the structured questions can be stored in a database or repository, such as data repository 202, and be stored by category, such as disease category (e.g. cancer, diabetes), treatment category (e.g. immunotherapy, chemotherapy), etc. For each category, questions can be defined in order to acquire needed patient reported data. In certain implementations, questions can have pre-conditions that are met for a question to be selected for conversation with a patient. Questions can have an identifier or ID number and be given a priority number.

Questions can be categorized to align with a medical term or program (e.g., treatment program), where there can be multiple programs. Examples of programs can include chemotherapy, radiation therapy, immunotherapy, surgery, targeted therapy, hormone therapy, etc. In certain implementations, a program category, for example immunotherapy or IO, can be defined by a DTx knowledge model which can include categories such a "primary symptoms", "secondary symptoms", "clinical modifiers", "laboratory tests", "imaging studies" etc. In certain implementations, such DTx knowledge models can determine symptom scores and an overall score for the questions, and the DTx knowledge models can be used as criteria for selecting questions from a list of total questions. In certain implementations, medical or disease experts as further described below, can author, group, and provide attributes for questions.

In certain implementations, such as through the detect component 218 and recommend component 220 as described below, a category of questions can be identified, and the dialog component 212 can modify or reduce the potential list of questions to actual questions that are presented to patient(s) 224. The recommend component can provide recommendations from the primary symptoms and laboratory results for addressing adverse events and related to the longitudinal data, deep layer patient profile (DLPP), and knowledge models. Recommendations can be derived from algorithms that use the patient answers, the laboratory results and the knowledge models. Furthermore, the recommendations can be derived by algorithms that use detect and diagnosis results, and produced preliminary diagnosis, priorities and weights.

Reducing/refining the questions can proceed as follows. A number of questions are selected from a current category. A number of questions are increased based on detected characteristics processed by artificial intelligence (AI) which can include sentiment analysis (elated, happy, sad, angry), voice changes (faster, slower, louder, quieter), image changes (facial lines, weight loss, growing rash), etc. Questions can be increased by aligning AI characteristics to a question pool and retrieving additional questions. Questions can be reduced to only include questions for a current symptom (e.g., blood, diarrhea, headache, etc.). Questions can be sorted in priority order. Questions can be presented in a priority order, such that certain questions can take precedence over other questions in diagnosing/evaluating patient(s) 224. The next question, if available, can be ensured to have a category related to the previous question, such that questions are asked in appropriate groups of symptoms. A question can be removed, if the same question is asked within a time window of question attribute frequency. A question can be included, if an "alert" indicates a question is to be repeated. A question can be removed, if preconditions have not been met. A question index number can be converted to match a request genre of questions, such as talking to a child versus talking to an elderly person, talking in a dialect versus talking in a standard language, talking with text versus pictures versus audio, etc. A question index number can be used to retrieve a question in a correct language (e.g., English, Chinese, Spanish, etc.).

The health AI environment 200 can include developers 230 who provide and modify applications and software modules, such as components 212, 214, 216, 218 and 220. Developers 230 can create and update DTx knowledge models used in the digital therapeutics or DTx. Developers 230 can provide and update questions, rules and actions as to the DTx knowledge models. Developers 230 can connect to various entities of the health AI environment 200 and exchange information through devices 232. As used herein, a device 232 refers to an information handling system such as a personal computer, a laptop computer, a tablet computer, a personal digital assistant (PDA), a smart phone, a mobile telephone, or other device capable of communicating and processing data. Devices 232 can be connected to network 140, and in certain implementations are connected to secure networks and devices that are included in the network 140.

The health AI environment 200 can include disease or medical experts 234 who provide input updates in the development of applications and software modules, such as DTx knowledge models. Medical experts 234 can use the authoring tool 222 to author, group and provide attributes as to patient questions. In certain implementations, medical experts provide rules as used in by detect component 218. The detect component 218 can process and present primary symptoms with associated detect knowledge models as related to the longitudinal data and deep layer patient profile (DLPP). Medical experts 234 can connect to various entities of the health AI environment 200 and exchange information through devices 236. As used herein, a device 236 refers to an information handling system such as a personal computer, a laptop computer, a tablet computer, a personal digital assistant (PDA), a smart phone, a mobile telephone, or other device capable of communicating and processing data. Devices 236 can be connected to network 140, and in certain implementations are connected to secure networks and devices that are included in the network 140.

The health AI environment 200 can include health care providers 238 who assist in treating patients 224. Examples of health care providers 238 can include physicians, nurses, laboratory/diagnostic facilities, entities providing treatment, etc. In specific, health care providers 238 make use of digital therapeutics or DTx for patients 204. As discussed above, DTx can be independently implemented, or can be used with medication, medical devices, and other therapies to optimize care and treatment results for patients 224. Health care providers 238 can connect to various entities of the health AI environment 200 and exchange information through devices 240. Medical experts 234 and health care providers 238 can present physician results with associated diagnostic knowledge models as related to the longitudinal data and deep layer patient profile (DLPP). In certain implementations, health care providers 238 through devices 240 interact with diagnose component 216, detect component 218, and recommend component 220. As used herein, a device 236 refers to an information handling system such as a personal computer, a laptop computer, a tablet computer, a personal digital assistant (PDA), a smart phone, a mobile telephone, or other device capable of communicating and processing data. Devices 236 can be connected to network 140, and in certain implementations are connected to secure networks and devices that are included in the network 140.

In certain implementations, the health AI environment 200 includes a health data repository 242, which can include various data stores, databases, etc. The health data repository 242 and data and information stored therein can be made available to various entities of health AI environment 200, including the information handling system 100, and specifically the E-Combination digital therapy module 120. The health data repository 242 can be connected to the network 140, and to secure and unsecure networks of network 140.

Health data repository 242 can include electronic health records (EHR) 244. EHR 244 can include health information of patients 204. For example, health information can include administrative information, progress data, demographics of the patient, medical history, previous and prior diagnoses, medications of the patient, immunization record, allergies of patient, radiology and laboratory information, test results, etc. In addition, EHR 244 can include electronic medical records or EMR. An EMR can be considered a subset of an EHR, where the EMR can include specific information for a patient from a particular physician or clinic. An EMR can track data over time, identify particular patients for treatment, check patients' status based on certain parameters, such as blood pressure, etc.

The dialog component 212, transform component 214, diagnose component 216, detect component 218, and recommend component 220 are further described. It is to be understood that implementation of the invention, including the components, may be implemented entirely in hardware, entirely in software (including firmware, resident software, micro-code, etc.) or in an embodiment combining software and hardware.

The dialog component 212 can present to patient(s) 224, a refined list of questions, which are answered by the patient(s) 224. The questions can be stored in a database, such as data repository 202, and can be stored by category (e.g., diabetes, immunotherapy, chemotherapy, or other disease category). The question categories can align with medical term program, where multiple programs can be supported. For each category, the questions can be defined in order to get needed patient reported data. Questions can also have pre-conditions that are met in order for questions to be selected for conversation with a patient(s) 224. Questions can have an identifier (ID) and a priority number.

In certain implementations, a program category (e.g., immunotherapy) can have a defined DTx knowledge model that includes primary symptoms, secondary symptoms and clinical modifiers, etc. The DTx knowledge model can determine symptom scores and an overall score. The DTx knowledge model can be used as criteria for selecting questions out of the total list of questions. The authoring tool 222 can be used by medical experts 234 to author, group and provide attributes for questions.

As discussed above, the dialog component 212 can interact with patient(s) through various entry points, such as a mobile phone application, tablet application, web browser, smart mirror, microphone, camera, fixed and moveable robotics, personalized cameras, human delegate, etc. When the dialog component 212 and the recommend component 220 identify a category of questions, the dialog component 212 can intelligently modify/reduce a potential list of questions to actual questions. Refining the questions by the dialog component is described in detail above.

The transform component 214 can transform answers to questions into longitudinal data. Longitudinal data being repeated observational data using the same variable over various times. In certain implementations, such longitudinal data can be digital deep layer patient profile (DLPP) (e.g., deep layer patient profile (DLPP) 204). By implementing DTx knowledge models and medical systems, if a symptom has an identifier (ID) for data that is being collected (e.g., rash color), the data (e.g., rash color) is attached to a question or answer. When questions are answered, the data can be added to longitudinal data for the identifier (ID) for the data with a timestamp. The questions can have N answers, where each answer can be mapped to a different identifier (ID). Each answer has an answer type (e.g., text, image, number, voice). Primary symptoms can be produced from algorithms using patient reported symptoms and the subject matter expert knowledge models. In certain implementations, natural language patient reported symptoms, disambiguating patient reported outcomes with dialog techniques, and producing a numerical longitudinal mapping for structured and deep layer patient profile (DLPP) storage are provided.

The text classifier 210 can convert mime types to text or data type that are stored. The type related to an answer can indicate how to store data. The data can be a tuple (i.e., finite ordered list), such as value/duration, and includes a timestamp. For example, if blood is found in stool, the tuple is (blood, stool). The detect component 218 can also generate longitudinal data. For example, if value/duration, duration of how long value has been going on.

The transform component 214 can update a deep layer patient profile (DLPP), which can be used to record patient responses, patient recorded outcomes, and other data. In certain implementations, the deep layer patient profile (DLPP) can be used for artificial intelligence (AI) analytics and searching.

A deep layer patient profile (DLPP) is a mechanism to turn related and structured patient data into a multidimensional unstructured data format that is processed with machine learning and image processing algorithms. Instead of selecting data, for example, by patient id, date, and data types needed, a deep layer patient profile (DLPP) is used for searching for intensity values that match thresholds. In certain embodiments, the deep layer patient profile (DLPP) is also anonymized from the original data source and thus can be shared without privacy concerns. The deep layer patient profile (DLPP) after anonymization, can be manipulated with completely new algorithms focused on binary and intensity operations, such as image processing and deep learning.

In certain embodiments, the deep layer patient profile (DLPP) is created, updated and accessed using the following mappings: time—using 24 bits for Julian date; patient symptom—assigned 1 to assigned 1 to N in 24 bits for 16 M possible values, related to patient response; condition—assigned 1 to N in 24 bits for 16 M possible values; severity score—assigned 1 to N in 24 bits for 16 M possible values, related to patient response transformed to business implementation representation; symptom (S), condition (C), specific collection of symptoms, overall; heart rate, blood pressure (BP), that can also be grouped/mapped to scores (e.g., 90-95=>3); Common Terminology Criteria for Adverse Events (CTCAE) grade from 1 to 5 (in 24 bits), where 1—Mild, 2—Moderate, 3—Severe, 4—Life-threatening, 5—Death; priority—0 to 4 in 24 bits; recommendation—1 to N in 24 bits. Optional: Labs, medications, conditions (problems), observations, etc. encoded each in 1 to N in 24 bits.

Slice and match to 24 bits can be shown as numeric, color pixel, intensity pixel. Each of these mapping values can be represented by another dimension in the deep layer patient profile (DLPP). The deep layer patient profile (DLPP) enables longitudinal data (all of the aforementioned mappings timestamped) by providing a time dimension.

Figure 3A:
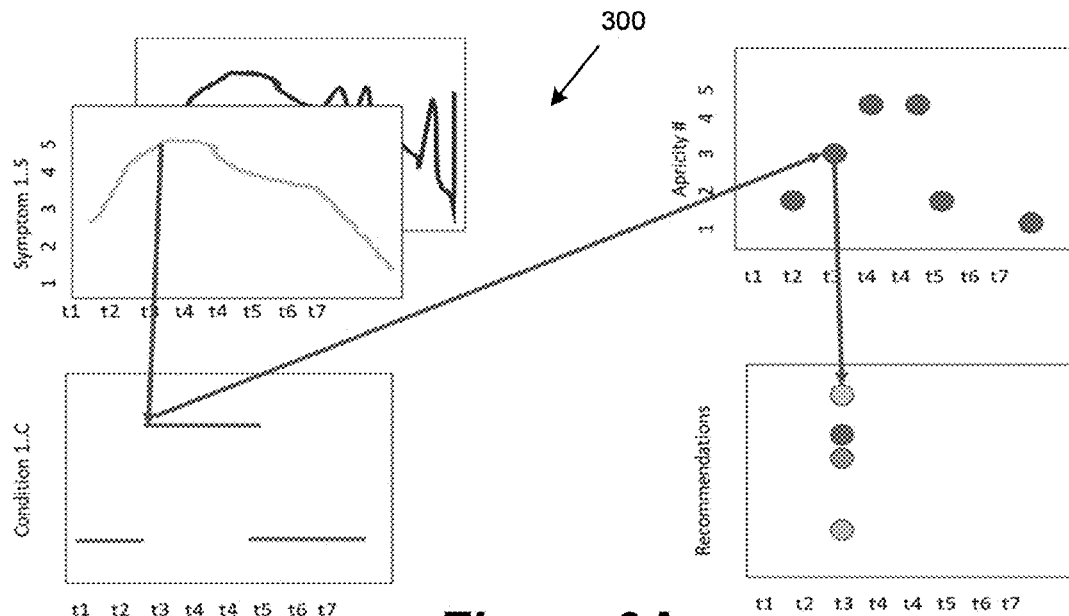
FIGS. 3A-3E show images representing a digital deep layer patient profile (DLPP)

FIG. 3A shows an example of a view 300 of structured patient profile symptoms related to conditions and then related to Score and how these combined values can be mapped to intensities in a deep layer patient profile (DLPP). In this example, at time t3, multiple symptoms, conditions and scores are given unique intensity mappings. Determining a unique value can be a 1 to 1 mapping between the sum of the available value ranges of structure items to an intensity value of 0 to the sum of ranges. More complex mappings are possible as in the case of needing only red, amber or green values, or, in the case of needing on gray scale values.

Figure 3B:
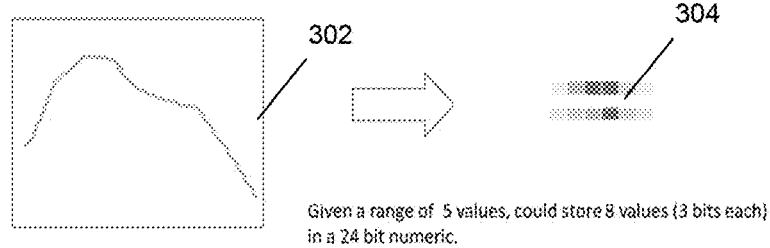

FIG. 3B shows an example of a longitudinal graph of symptoms that is mapped to a straight line with intensities. When mapping longitudinal data 302, the time dimension can be incremented, and additional intensities are added 304.

Figure 3C:
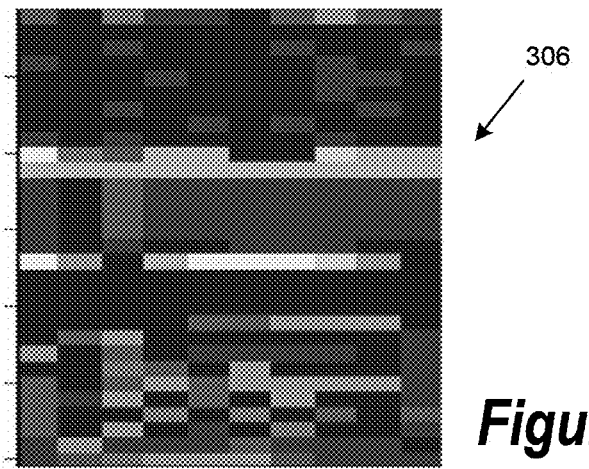

FIG. 3C shows an example user interface view 306 of a patient profile. As a deep layer patient profile (DLPP) is updated, it produces a patient signature. The patient signature can be "viewed" with multiple perspectives. A common perspective is to view the patient profile in a user interface view on a computing screen 306. The user interface view 306 shows time at the bottom horizontal access and various values from N other dimensions stacked on top. In certain implementation, the user interface view 306 becomes a patient's quick response (QR) code/ink blot identifier. In certain implementations, the deep layer patient profile (DLPP) can be optimally used for performing artificial intelligence/machine learning algorithms, such as with Python, OpenCV, Node, etc.

Figure 3D:
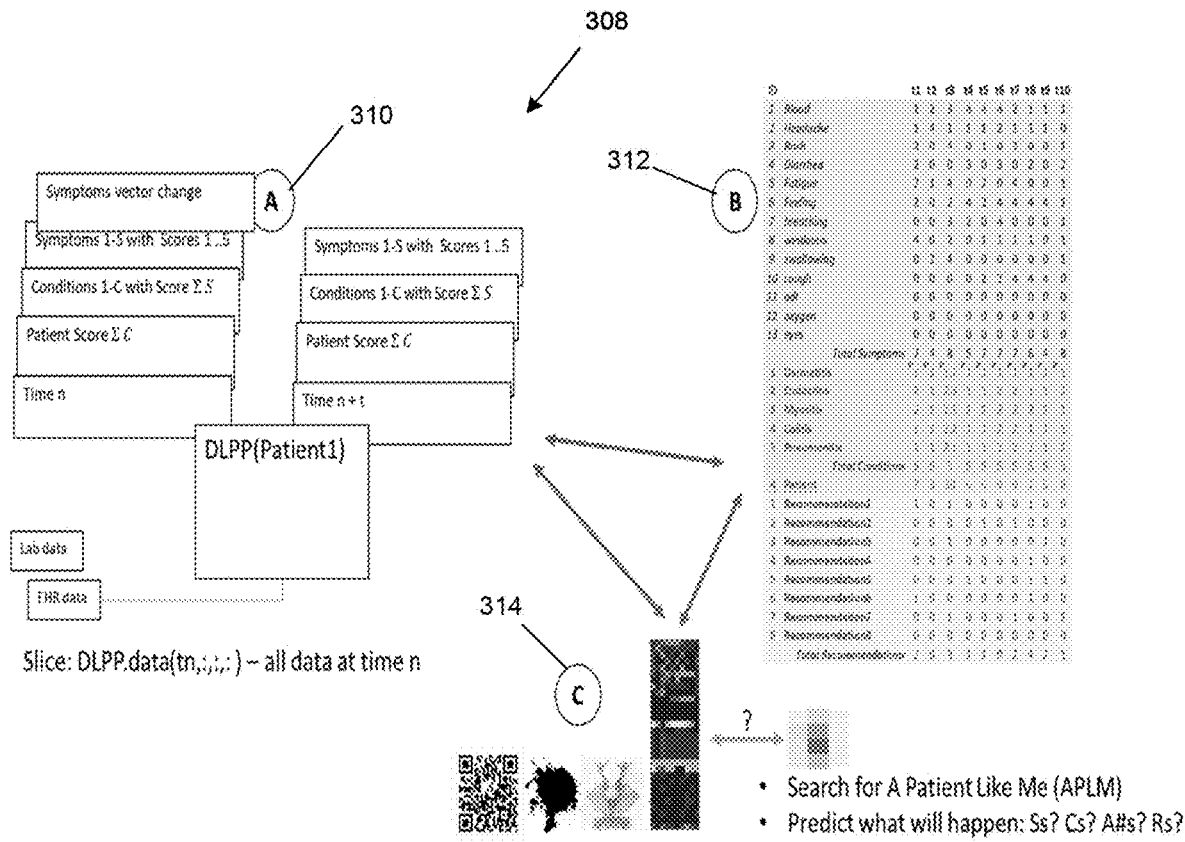

FIG. 3D shows an example process of development and use 308 of deep layer patient profile (DLPP). At "A" 310, dimensions are shown as used in a particular deployment of a deep layer patient profile (DLPP). The values per recording of patient data are shown in the formulas or variables. For example, Conditions 1 through C can have a score value of the summation of the symptom scores. Additionally, slope (i.e., change in intensity) or derivatives (i.e., change in change) can be calculated. The rules indicated are related to patient report data. Lab data and electronic health record data can also be used to update reported data. For example, an N dimensional region of the DLPP can be referred to as a "slice" and uses Python notation (e.g., range dimension 1, range dimension 2, . . . range dimension N). The deep layer patient profile (DLPP) becomes a patient's longitudinal representation: DTx+drug therapy=precision and personalized care pathway.

"B" 312 shows a structured recording of patient profile over time t1, t2, . . . tn. As previously mentioned, each value recorded that is part of a deep layer patient profile (DLPP) is mapped to an intensity value. In section be, time t3 (column t3) shows raw intensity values. Raw values, such as 1 . . . 5, can be scaled to wider values, such as 1 . . . 255, to allow more visual distinction when using a user interface perspective. Additional values can be included such as summation, mean, standard deviation, mode, median, and outliers.

"C" 314 shows the user interface view of a deep layer patient profile (DLPP) contain mapped data. As mentioned, a user interface is one perspective (or view) on a deep layer patient profile (DLPP). Other perspectives include, but are not limited to, binary arrays, gray images and animations of intensities over time. The animation, in particular, can be a standard graph animation, or a geolocation animation where the intensity type is animated over a 3D human body outline.

When using array views, slice and searching may be possible using ML and image processing algorithms. When using these algorithms, there may be no real indication that the included data is patient health data. Rather, algorithms such as movement detection, line detection, object detection, histogram analysis, rotation, translation, shear, thresholding, blurring, erosion, dilation, contouring, etc. can be used.

The deep layer patient profile (DLPP) can be a gateway between structured and protected patient health data, and, intensity based on data upon which to perform high performance AI algorithms. A N dimensional region of a deep layer patient profile (DLPP) can be compared against other regions, such as is the case when comparing different time regions. A N dimensional region of a deep layer patient profile (DLPP) can be compared to a region of another patient, such as is the case when searching for "a patient like me."

When performing these AI/ML algorithms, it may be the case that a 'good patient' or 'good data set' is needed. The good data sets are those deep layer patient profiles (DLPP) where the outcome was successful—the best case being the patient is cured of the disease. Having good data sets allows Detect, Diagnose, to create inferred and probabilistic recommendations based on patching a current patient from time t1 to tn to other patients who have survived from time t1 to tn+K, where K is more time past where the current patient is. Time tn to tn+K are where next irAEs, recommendations, lab tests or questions will 'probably' be needed or addressed by the current patient.

Figure 3E:
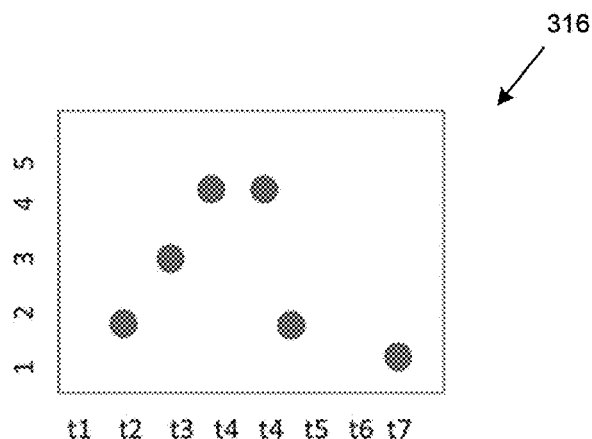

FIG. 3E shows a goal outcome 316. Outcome 316 describes a set of longitudinal data, DLPP images, recommendations/treatments that indicate adverse events is/has been removed. In specific, outcome 316 shows a combination of longitudinal paths, plus other data, where the trends approach "0" indicating that cancer has been removed. There can be various conditions that are considered as good. With enough good paths that are capture, it may be practical to pattern match a current "patient A" to search for similar paths. It may be possible to show that "patient A" with "confidence J" of next likely symptoms, conditions, trends, severity score, recommendations, etc.

Other approaches to encoding patient data can be CTS-CAN/MRI 3D views that are sliced but where data is homogenous (i.e. all about neck, pixels) and geographically close. Semantics may be known at the beginning, such as taking a scan of the neck to look for new data based on values scanned (i.e. tumor in neck).

DLPP data may be multi-type and not homogenous and geographically disperse. For example, reported blood lower abdomen, fever in head, and rash on arm, etc. The semantics may not be known at the beginning. A determination may be made as toxicity, where a patient has cancer and is under toxic treatment based on reported data, expert authored models, and treated under a DTx platform. However, previously known toxicity effects, patient reports, or where/ when irAE occurs are not known. Semantics can be derived, and then intensity values are derived, such as to display as pixels in a user interface.

DLPP can include primary data, such as patient reported, lab, EHR, social (e.g., family, wealth, etc.), environment (e.g., altitude, seasons, etc.), energy (movement, exercise, diet, etc.) and symptoms as represented by vector of change. The DLPP can include secondary data, such as score, grading, counts, vector of change, determined conditions, score number, CTCAE score, etc. Furthermore, DLPP can include tertiary data, such as using primary and secondary data with expert knowledge leading to recommendations. The DLPP can use quaternary data, such as AI/ML algorithms, image processing and pattern matching across primary/secondary/tertiary data. Values can be replaced (i.e. what if next 2 days were these results), then match is performed.

Data progression can occur as DTx AI/ML systems and experts process data. Raw data can be provided by a patient or device (e.g. Yes/No; blood pressure 150/99). Information data may be context to the raw data (e.g. patient indicated a fever). Knowledge data can add additional context and experience to information data (e.g. patient having AE to medicine; patient has flu). Derived data can add analytics to knowledge, information and raw data (e.g. average fever using medicine, % chance fever reduces in N days). Inferred data can add AI/ML to derived, knowledge, information and raw data to generate additional deterministic data (e.g. based on 1000 patients like current patient, reduce medicine 50%). Probabilistic data can add AI/ML to the aforementioned data to generate additional probability confidence data (e.g. 80% probability patient will escalate AE if medicine continued at 100%; 90% confident that current medication with two other medications will not reduce disease). DLPP can contain all data progression levels as longitudinally included.

Now referring back to FIG. 2, in certain implementations, the transform component 214 can include an ambiguity layer for uncertain, vague or subjective responses from patients 224. The ambiguity layer can translate subjective non-standardized responses into objective standardized responses. As an example, two patients 224 indicate a headache level 4; however, the pain threshold may be different between the two patients 224. Therefore, a follow up question can be related to negative effects of the headache. For example, did you go to work? If one patient says no, there can be some level of assurance that the headache is debilitating and prevented the patient from working.

The diagnose component 216 can be invoked when deep layer patient profile (DLPP) updates are received from EMR, third party systems and lab results. Examples of such deep layer patient profile (DLPP) updates include lab results, x-ray results, blood work results, etc. The dialog component 216 can process and present laboratory results with associated diagnostic knowledge models as related to the longitudinal data and deep layer patient profile (DLPP). The diagnose component 215 can then provide additional recommendations based on the detect component 218 recommendations. The diagnose component 216 can confirm results, such as lab results (e.g., low blood count, colitis, etc.) The diagnose component 216 can provide treatment recommendations. Receiving a lab result can trigger the diagnose component 216. A difference between the diagnose component 216 and the detect component 218 is that the source of data for the diagnose component 216 includes lab test results, imaging studies, or procedures (clinical data) versus the source of data for the detect component 218 is patient provided data/outcomes (non-clinical data). In addition, the diagnose component 216 and the detect component 218 can use different or overlapping DTx knowledge models.

The detect component 218 can filter out symptoms and rule out patient reported outcomes (PRO). The detect component 218 can be invoked by the transform component 214 after the dialog component 212 invokes the transform component 214. Deep layer patient profile 204 can be sent to the detect component 218. The detect component 218 can also access the data repository 202 for any other relevant information.

The detect component 218 can load primary symptoms with associated symptom knowledge models. The detect component 218 can run detection rules, where such rules can be authored by medical experts 234 and provided in a table of rules. The following tables are examples of such rules.

| Colitis; primary = bmFreq, bloodAmount | | | | | | | | |
|---|---|---|---|---|---|---|---|---|
| CTCAE Grade | Grade 0 | Grade 1 | | Grade 2 | | Grade 3 | | Grade 4 |
| Alert Color | green | yellow | | | | red | | |
| Evaluation Priority | 0 | 1 | | 2 | | 3 | | 4 |
| Primary Symptoms | 0 for all | 1 on any | 1 on any | 2 on any | 2 on any | 3 on any | 3 on any | 4 on any |
| Associated Symptoms | 0-4 for all | 0-2 for all | 3 on any | 0-2 for all | 3 on any | 0-2 for all | 3 on any | 0-3 for all |

| Dermatitis; primary = rashCoverage | | | | | |
|---|---|---|---|---|---|
| CTCAE Grade | Grade 0 | Grade 1 | Grade 2 | Grade 3 | Grade 4 |
| Alert Color | green | | yellow | | red |
| Evaluation Priority | 0 | 1 | 2 | 3 | 4 |
| Primary Symptoms | 0 for all | 1 on any | 2 on any | 3 on any | 4 on any |
| Associated Symptoms | 0-4 for all | 0-4 for all | 0-4 for all | 0-2 for all | 3-4 on any | 0-4 for all |

| Endocrine; primary = fatigueOrMalaise, headache, dizzyOrFainting | | | | | |
|---|---|---|---|---|---|
| CTCAE Grade | Grade 0 | Grade 1 | Grade 2 | Grade 3 | Grade 4 |
| Alert Color | green | | yellow | | red |
| Evaluation Priority | 0 | 1 | 2 | 3 | 4 |
| Primary Symptoms | 0 for all | 1 on any | 2 on any | 3 on any | 4 on any |
| Associated Symptoms | 0-4 for all | 0-4 on any | 0-4 on any | 0-4 on any | 0-4 on any |

| Pneumonitis; primary = shortOfBreath, coughSeverity, oxygen, oxygenWalking | | | | | | | | |
|---|---|---|---|---|---|---|---|---|
| CTCAE Grade | Grade 0 | Grade 1 | | Grade 2 | | Grade 3 | | Grade 4 |
| Alert Color | green | yellow | | | | red | | |
| Evaluation Priority | 0 | 1 | | 2 | | 3 | | 4 |
| Primary Symptoms | 0 for all | 1 on any | 1 on any | 2 on any | 2 on any | 3 on any | 3 on any | 4 on any |
| Associated Symptoms | 0-4 for all | 0-2 for all | 3-4 on any | 0-2 for all | 3-4 on any | 0-2 for all | 3-4 on any | 0-4 for all |

| Uveitis; primary = visionChanges, eyePain | | | | | |
|---|---|---|---|---|---|
| CTCAE Grade | Grade 0 | Grade 1 | Grade 2 | Grade 3 | Grade 4 |
| Alert Color | green | | yellow | | red |
| Evaluation Priority | 0 | 1 | 2 | 3 | 4 |

Uveitis; primary = visionChanges, eyePain

| CTCAE Grade | Grade 0 | Grade 1 | | Grade 2 | | Grade 3 | Grade 4 |
|---|---|---|---|---|---|---|---|
| Primary Symptoms | 0 for all 0-4 | 1 on any 0-2 | 1 on any 3 | 2 on any 0-2 | 2 on any 3 | 3 on any 0-3 | 4 on any 0-3 |
| Associated Symptoms | for all | for all | on any | for any | on any | for all | for all |

For example, for primary symptoms, ALL (meaning AND) or ANY (meaning OR of 1 or more) of the primary symptoms grading score have been met. Patients 224 can report symptoms in grades, for example 0 to 4 for severity of blood. Grading scores determine level of symptom. Symptoms can be evaluated in right to left order in Table and indicated by evaluation number. If primary symptom is met (i.e. ALL or ANY evaluates to True) then evaluation associated symptoms are also, both primary and (associated symptoms OR clinical modifier) are True.

The detect component 218 further evaluates symptom scores for each category (e.g. Myositis, Dermatitis, Pneumonitis, etc.). Scores can be calculated from a SUM of (severity grade×weights). Patient 224 can define the grade, medical experts 234 using the authoring tool 222 can define weights. Scores not with Table guidelines can be filtered out. Filtered questions will not be used. Common Terminology Criteria for Adverse Events or CTCAE are a set of criteria for the standardized classification of adverse effects of drugs used in cancer therapy. CTCAE uses a range of grades from 1 to 5. Specific conditions and symptoms may have values or descriptive comment for each level, but the general guideline is "1" for mild, "2" for moderate, "3" for severe, "4" for life threatening, and "5" for death. The scores can include CTCAE grades along with the scores determined by the digital therapy module 120. The CTCAE grade is per system area, while the scores determined by the digital therapy module 120 is a sum of all scores.

The detect component 218 can look at trends of CTCAE grade or sum of scores over time (longitudinal) and determine if a "alert" should be set to further in the questions to patient 224. The detect component 218 can store scores in journal 208 (data repository 202). Authorized parties can view the journal 208. The detect component 218 can invoke the recommend component 220.

The recommend component 220 provides a set of recommendations for treatment. When invoked by the detect component 218, the recommend component 220 can retrieve context or deep layer patient profile (DLPP) 204. The recommend component 220 can load actions from the data repository 202 for programs that patient 224 is associated with. The recommend component 220 can run each action and test for pre-conditions. If a pre-condition is true, then tasks associated with the action are executed. Tasks can notify provider 238, add a recommendation, add longitudinal data, add follow up, notify patient 224, order a medical test for patient 224. The recommend component 220 can build a collection of action results. The recommend component 220 can run through the recommendations and relate each to a group ID (e.g. group IO therapy) and get a recommendation to continue and discontinue at the same time. The higher the priority of a recommendation will override a lower priority of a recommendation. The recommend component 220 can provide traceability of conflicting recommendations for health care providers 238. Conditions that led to the recommendation can be attached on the recommendation.

The recommend component 220 can determine what knowledge model and the level of the knowledge model the recommendation came from. Recommendations can be weighted, for example a weight of "1" can indicate it is required by the health care provider 238, where a weight of "0" may mean it is optional. A health care provider 238 may require provider 238 indicate that they complied with the recommendation or check that the recommendation was followed. Recommendations can be written to the data repository 202. Deep layer patient profiles (DLPP) 204 and context can be supplemented with recommendations and provided to the detect component 218 and used by the dialog component 212.

To illustrate the use of knowledge models, the following example is described. In the domain of oncology, one program can be IO treatment related adverse event management. As discussed above, other examples of programs can include chemotherapy-related, radiation therapy-related, targeted therapy-related, hormone therapy-related adverse event management, etc. A set of knowledge models defines a program. A set of questions, rules and actions are provided for the program. Certain knowledge models are applicable to certain components of the digital therapy module 120. The knowledge models are defined by variables, weights and values, and other factors.

In this example, for knowledge models of the detect component 218, a "trigger" is a symptom that drives the knowledge model to be activated (e.g., rash for dermatitis, diarrhea for colitis, elevated liver function test results for hepatitis). A "primary symptom" is related to a priority, weights, and an ID (e.g., headache). An "associated symptom(s)" is related a priority, weights, and an ID (e.g., location, severity, etc. of the headache). A "clinical modifier" is related to a priority, weights, and an ID (e.g., had a prior irAE). For knowledge models of the diagnose component 216, clinical lab results drive the knowledge model to be activated (e.g., configured rash for dermatitis). A "primary symptom" is related to a priority, weights, and an ID (e.g., headache). An "associated symptom(s)" is related a priority, weights, and an ID (e.g., location, severity, etc. of the headache). A "clinical modifier" is related to a priority, weights, and an ID (e.g., had a prior irAE). For knowledge models of the recommend component 220, there can be pre-conditions based on rule, conditional, and time trends. A recommendation can be weighted by a health care provider 238 and identified.

Figure 4:
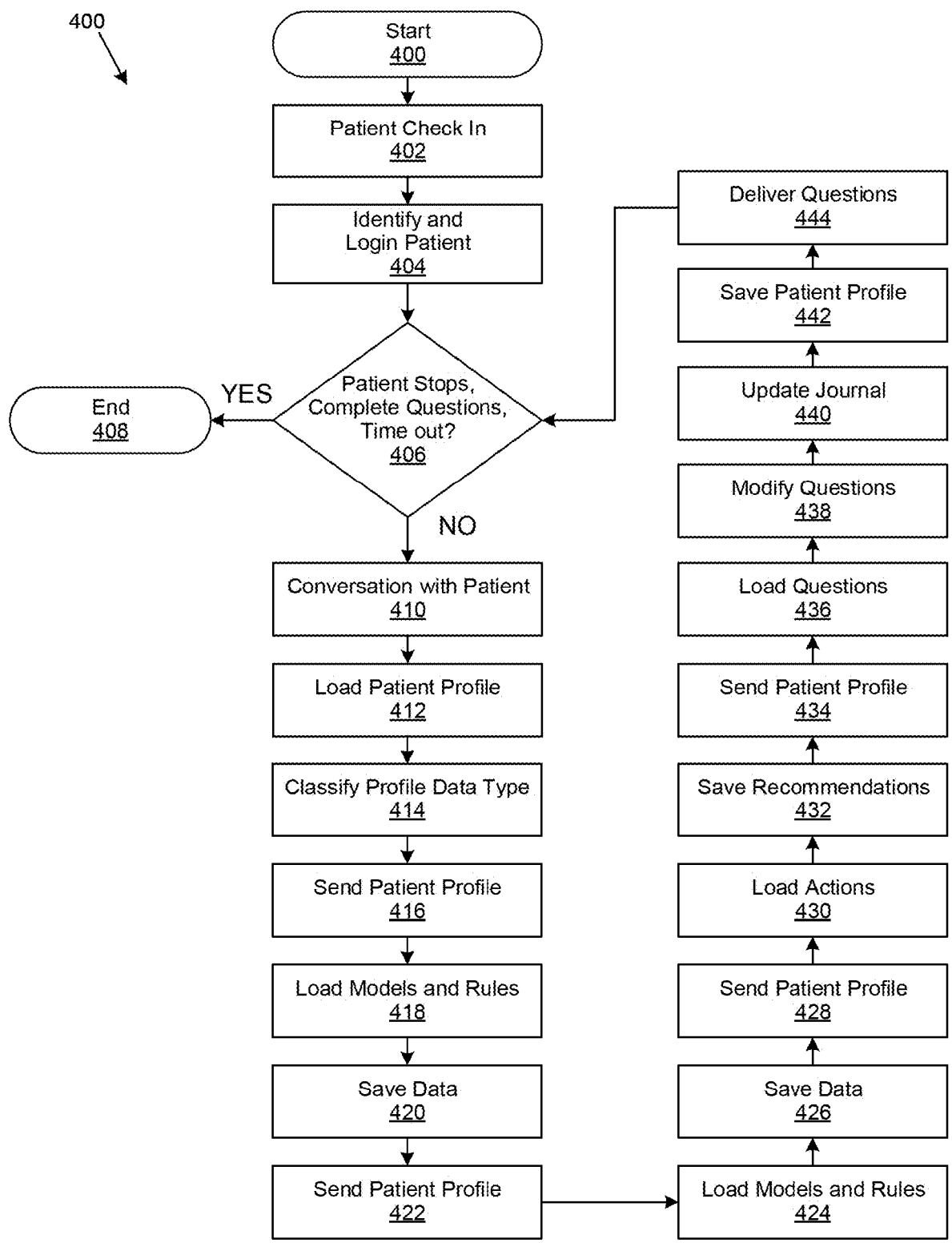
FIG. 4 shows a flowchart for patient conversation for digital therapeutics.

FIG. 4 is a generalized flowchart 400 for patient conversation for digital therapeutics. In various embodiments, the health AI system 118 is implemented. In particular, the process 400 can be performed during interaction with dialog component 212 of the digital therapy module 120. The order in which the method is described is not intended to be construed as a limitation, and any number of the described method blocks may be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 402 the process 400 starts. At step 402, a patient checks in. For example, patient(s) 224 through devices 226 invokes an application on devices 206 to connect with the information handling system 100, and in specific to the dialog component 212. At step 404, the patient is identified and logged in. For example, an ID related to the patient recognized by the dialog component 212 logs in the patient (s) 224.

If the patient decides to end the session, or if questions are completed, or if a session times out, then following the YES branch of block 406, the process 400 ends. Otherwise, following the NO branch of block 406, at step 410 conversation with the patient and the dialog component 212 begins or continues. For example, the conversation can include artificial intelligence (AI) generated questions form the dialog component 212 to the patient(s) 204.

At step 412, deep layer patient profile (DLPP) data is loaded. Deep layer patient profile data can include patient record(s), longitudinal data, current recommendations, state of the question process to the patient, question preferences, genre, etc. In certain implementations, the data repository 202 provides a specific deep layer patient profile (DLPP) to deep layer patient profiles (DLPP) 204. The dialog component 212 then loads the specific deep layer patient profile (DLPP). At step 414, the classification is performed on the deep layer patient profile (DLPP). For example, classification can be directed to format of the data, such as mime type as discussed above. In certain implementations, the dialog component 212 can invoke text classifier 210 to perform the classification.

At step 416, the deep layer patient profile (DLPP) is sent to the transform component 214. At step 418, knowledge models and rules are sent to the transform component 214. In certain implementations, the transform component 214 is used to create machine readable data from information such as patient answers to questions. In general, the transform component 214 can be implemented to provide data that is readable by the health AI system 118, and specifically the digital therapy module 120 and its components. In certain implementations, the authoring tool 222 provides the DTx knowledge models and rules to the transform component 214.

At step 420, data is saved. For example, the transform component 212 saves data to the data repository 202. At step 422, the deep layer patient profile (DLPP) is sent to the detect component 218. In certain implementations, the detect component 218 is used to filter out patient symptoms and rule out certain patient reported outcomes (PRO).

At step 424, knowledge components and rules are loaded. For example, the authoring tool 222 provides or loads knowledge components and rules to the detect component 218. At step 426, data is saved. In certain implementations, the data is saved from the detect component 218 to the data repository 202. At step 428, the deep layer patient profile (DLPP) is sent. The deep layer patient profile (DLPP) can be sent from the detect component 218 to the recommend component 220. At block 430, actions are loaded. For example, the actions are loaded from the data repository 202 to the recommend component 220. The recommend component 220 can provide a set of recommendations for treatment of the patient. In certain implementations, recommend component 220 is invoked by the detect component 218, and receives context or deep layer patient profile (DLPP), and loads and runs the actions for programs that the patient is associated with. At block 432, recommendations are sent. The recommend component 220 can send recommendations to be stored in the data repository 202.

At step 434, deep layer patient profiles (DLPP) are sent. In certain implementations, the recommend component 220 sends the deep layer patient profiles (DLPP) to the detect component 218. The detect component 218 sends the deep layer patient profile (DLPP) to the transform component 214. The transform component 214 sends the deep layer patient profile (DLPP) to the dialog component 214.

At step 436, questions are loaded. The data repository 202 can load questions to the dialog component 212. At step 438, the questions are modified. In certain implementations, the dialog component can modify the questions. At step 440, an update is performed on the journal 208. At step 442, an updated deep layer patient profile (DLPP) is saved. In certain implementation, the updated deep layer patient profile (DLPP) is saved from the dialog component 212 to the deep layer patient profiles (DLPP) 204, and the deep layer patient profiles (DLPP) 204 save the deep layer patient profile (DLPP) to the data repository 202.

At step 444, the questions are delivered to the patient. In certain implementations, the dialog component 212 provides the questions to a device 226 of user 224. The questions can be delivered through an application on the device 226. If the patient decides to end the session, or if questions are completed, or if a session times out, then following the YES branch of block 406, the process 400 ends. Otherwise, following the NO branch of block 406, the process 406 continues.

Figure 5:
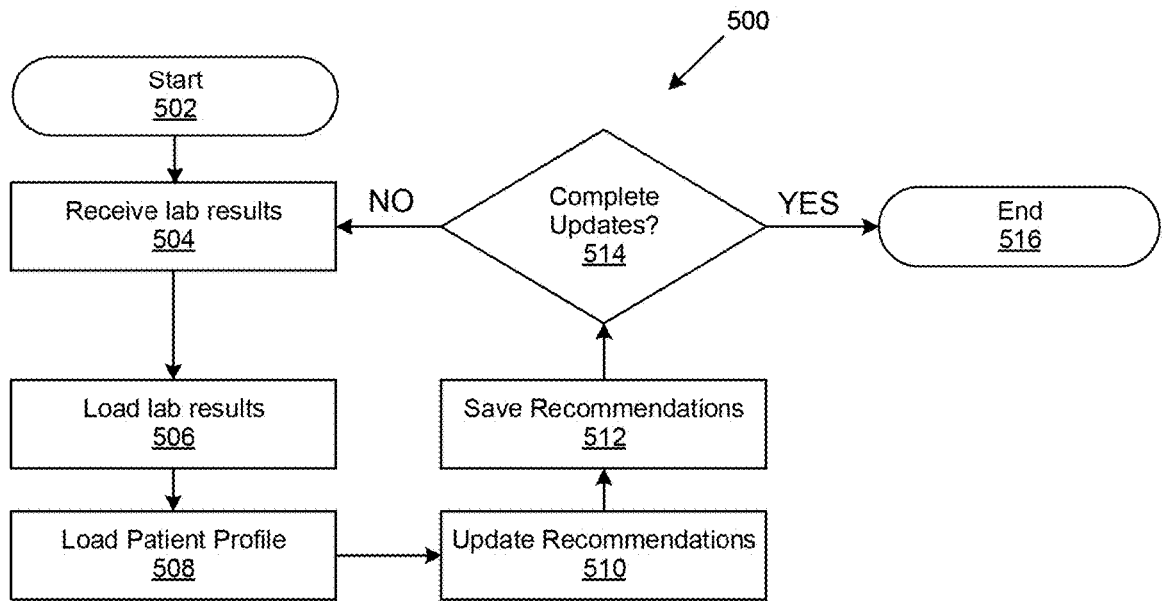
FIG. 5 shows a flowchart for patient updates.

FIG. 5 is a generalized flowchart 500 for patient updates. In various embodiments, the health AI system 118 is implemented. In particular, the process 500 can be performed during interaction with diagnose component 216 of the digital therapy module 120. The order in which the method is described is not intended to be construed as a limitation, and any number of the described method blocks may be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 502 the process 500 starts. At step 504, lab results are received. In certain implementations, lab results are made available at health data 242, and in the form of electronic health records (EHR) 244. The lab results can be received by the data repository 202. At step 506, the lab results are loaded. The lab result can be loaded from the data repository 202 to the diagnose component 216. At step 508, deep layer patient profile (DLPP) is loaded. The deep layer patient profile (DLPP) can be loaded from deep layer patient profiles (DLPP) 204 to the diagnose component 216. At step 510, recommendations are updated. The diagnose component 216 can update the recommendations to the recommend component 220. At step 512, recommendations are saved. The recommend component 220 can save the recommendations to the data repository 202. If the updates are complete, then following the YES branch of block 514, the process 500 ends at block 516. Otherwise, following the NO branch of block 514, the process 500 continues.

Figure 6:
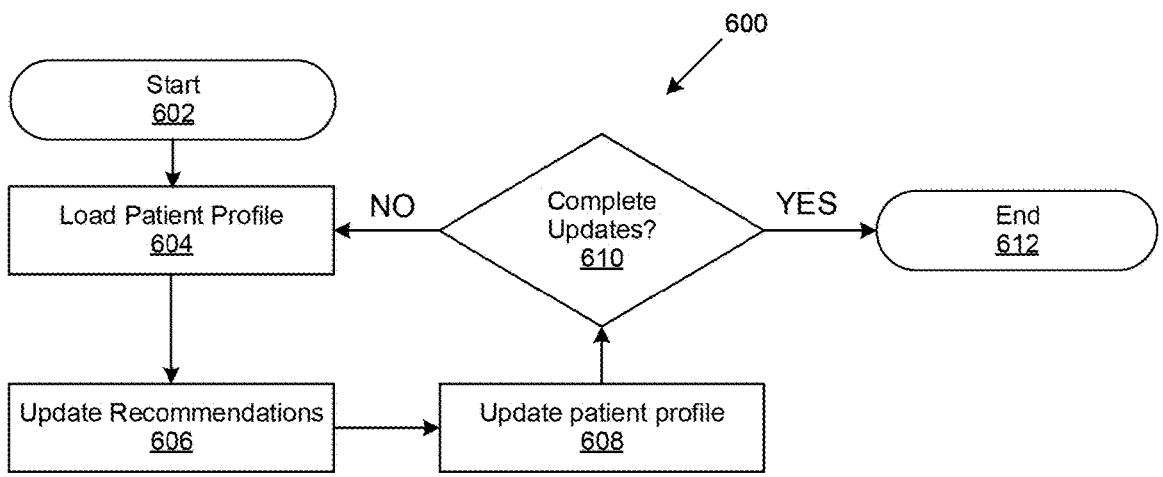
FIG. 6 shows a flowchart for provider updates.

FIG. 6 is a generalized flowchart 600 for provider updates. In various embodiments, the information handling system 100 is implemented. In particular, health care providers 238 through devices 240 interact with deep layer patient profiles (DLPP) 204 of the information handling system 100. The order in which the method is described is not intended to be construed as a limitation, and any number of the described method blocks may be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 602 the process 600 starts. At step 604, is loaded. In certain implementations, the deep layer patient profile (DLPP) is loaded from deep layer patient profiles (DLPP) 204 to a device(s) 240 of health care provider(s) 238. At step 606, recommendations are updated. The health care provider(s) 238 through device(s) 240 can update recommendations to the recommend component 220. At step 608, deep layer patient profile (DLPP) is updated. The health care provider(s) 238 through device(s) 240 can provide the updated deep layer patient profile (DLPP) to the deep layer patient profiles (DLPP) 204 of data repository 202.

Figure 7:
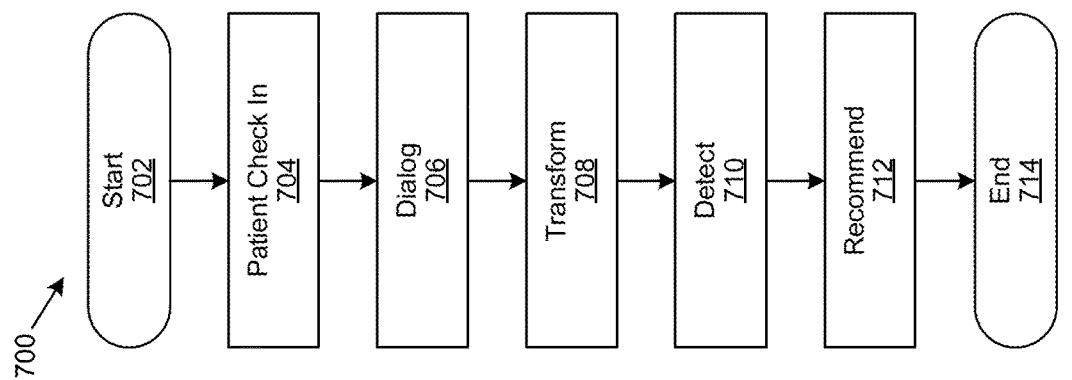
FIG. 7 shows a flowchart for patient conversation for a patient to submit patient symptoms.

FIG. 7 is a generalized flowchart 700 for a patient conversation for a patient to submit patient symptoms. In various embodiments, the information handling system 100 is implemented. The process 700 in general describes the interaction of the components of digital therapy module 120 when a patient 224 submits patient symptoms or patient reported outcomes (PRO). Throughout the process 700, as described above, DTx knowledge models, deep layer patient profiles (DLPP), questions, and rules can be implemented. At block 702, the process 700 starts. At step 704, a patient checks in. At step 706, the dialog component 212 is initiated. At step 708, the transform component 708 is initiated. At step 710, the detect component 218 is initiated. At step 712, the recommend component 220 is initiated. The process ends at block 714.

Figure 8:
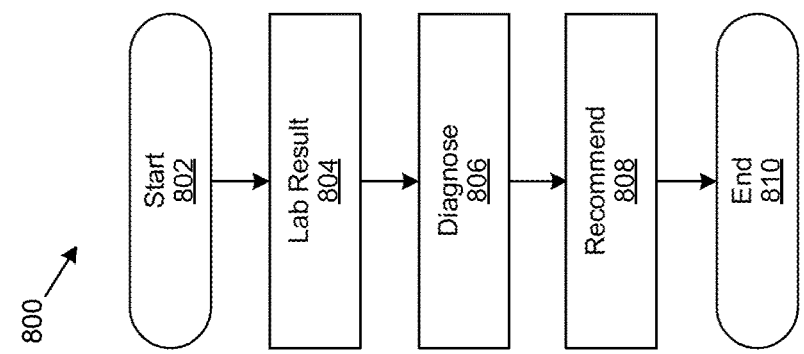
FIG. 8 shows a flowchart as to when an electronic medical record (EMR) or lab notification is received.

FIG. 8 is a generalized flowchart 800 as to when an electronic medical record (EMR) or lab notification is received. In various embodiments, the information handling system 100 is implemented. The process 800 in general describes the interaction of the components of digital therapy module 120 when a patient 224 receives an EMR or lab notification. Throughout the process 800, as described above, DTx knowledge models, deep layer patient profile (DLPP), questions, and rules can be implemented. At block 802, the process 800 starts. At step 804, a lab result or EMR is received. At step 806, the diagnose component 216 is initiated. At step 808, the recommend component 220 is initiated. The process ends at block 810.

Figure 9:
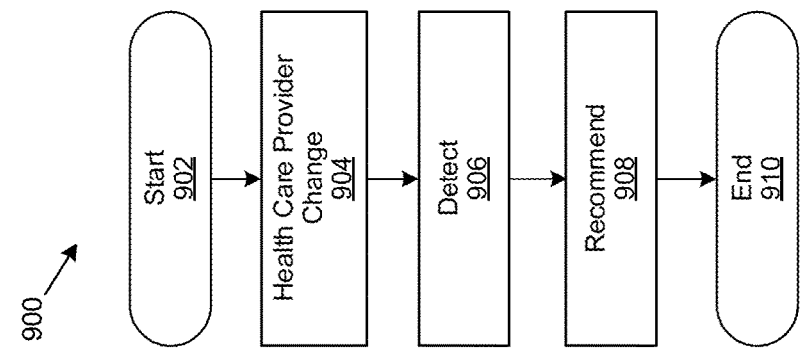
FIG. 9 shows flowchart as to when a health care provider changes data.

FIG. 9 is a generalized flowchart 900 as to when a health care provider changes data. In various embodiments, the information handling system 100 is implemented. The process 900 in general describes the interaction of the components of digital therapy module 120 when a health care provider 238 changes/modifies/adds patient related data. Throughout the process 900, as described above, DTx knowledge models, deep layer patient profiles (DLPP), questions, and rules can be implemented. At block 902, the process 900 starts. At step 904, a health care provider 238 makes a change to patient data. At step 906, the detect component 218 is initiated. At step 908, the recommend component 220 is initiated. The process ends at block 910.

Figure 10:
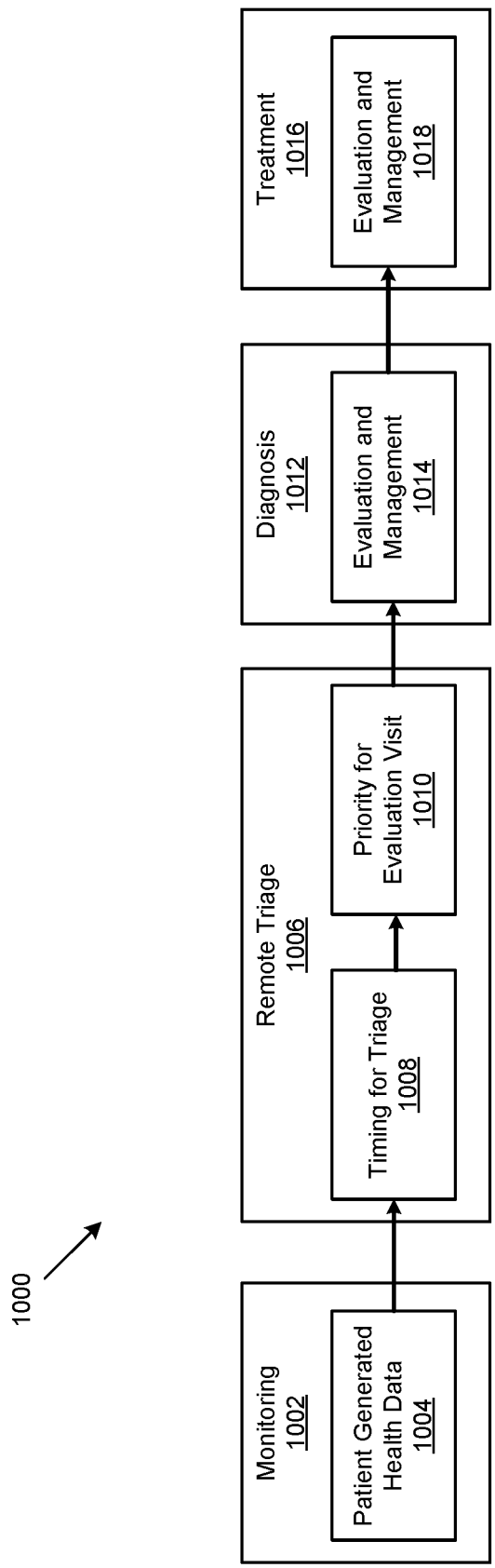
FIG. 10 shows a flow or care pathway for digital therapeutics.

FIG. 10 is an example method, flow or care pathway. Although depicted linearly, it is to be understood that the blocks can be performed in parallel, and that feedback from succeeding blocks can be provided to preceding blocks. A flow or care pathway 600 can be implemented as part of the digital therapeutics or DTx. Block 1002 performs patient monitoring. The monitoring block 1002 can be performed by patients 224 or delegates of patients 224. In specific, patent generated health data or PGHD 1004 is monitored. The PGHD 1004 can be self-reported symptoms such as patient reported outcomes (PRO). In certain instances, PGHD 1004 can be gathered through patient data monitoring/sensing devices 228, such as Bluetooth enabled biometrics that measure patient vital signs, such as oxygen.

Block 1006 performs a remote triage. The remote triage block 1006 can be video or voice, and be performed by care coordinators, such as nurses. Block 1008 is a timing for the triage. In specific, timing is related to urgency for treatment. For example, an indication or "red" can be immediate, "yellow" can be for the next day, and "green" can be for notification only. Block 1010 is directed to prioritization for an evaluation visit. For example, various levels can be implemented as to the priority, such as "P1" for emergent/immediate, "P2" for urgent/same day, "P3" for within 72 hours, "P4" for a watch list, and "P5" for a routine visit.

Block 1012 performs a diagnosis. The diagnosis block 1012 can be performed by health care providers 238, such as physicians. In certain implementations, an application can used by the health care providers 238. Block 1014 is evaluation and management which can provide for a diagnostic workup, such as exams/lab tests, procedures and imaging, consultation, etc. In addition, symptom management can be provided, such as care setting, supportive care, immunosuppressive prescriptions, etc.

Block 1016 performs treatment. The diagnosis block 1016 can be performed by health care providers 238, such as physicians. In certain implementations, an application can be used by the health care providers 238. Block 1018 is evaluation and management which can distinguish between inpatient versus outpatient evaluation and management, virtual versus in-person evaluation and management, provide for monitoring labs, provide 10 therapy status, provide immunosuppressive prescriptions, etc.

Figure 11A:
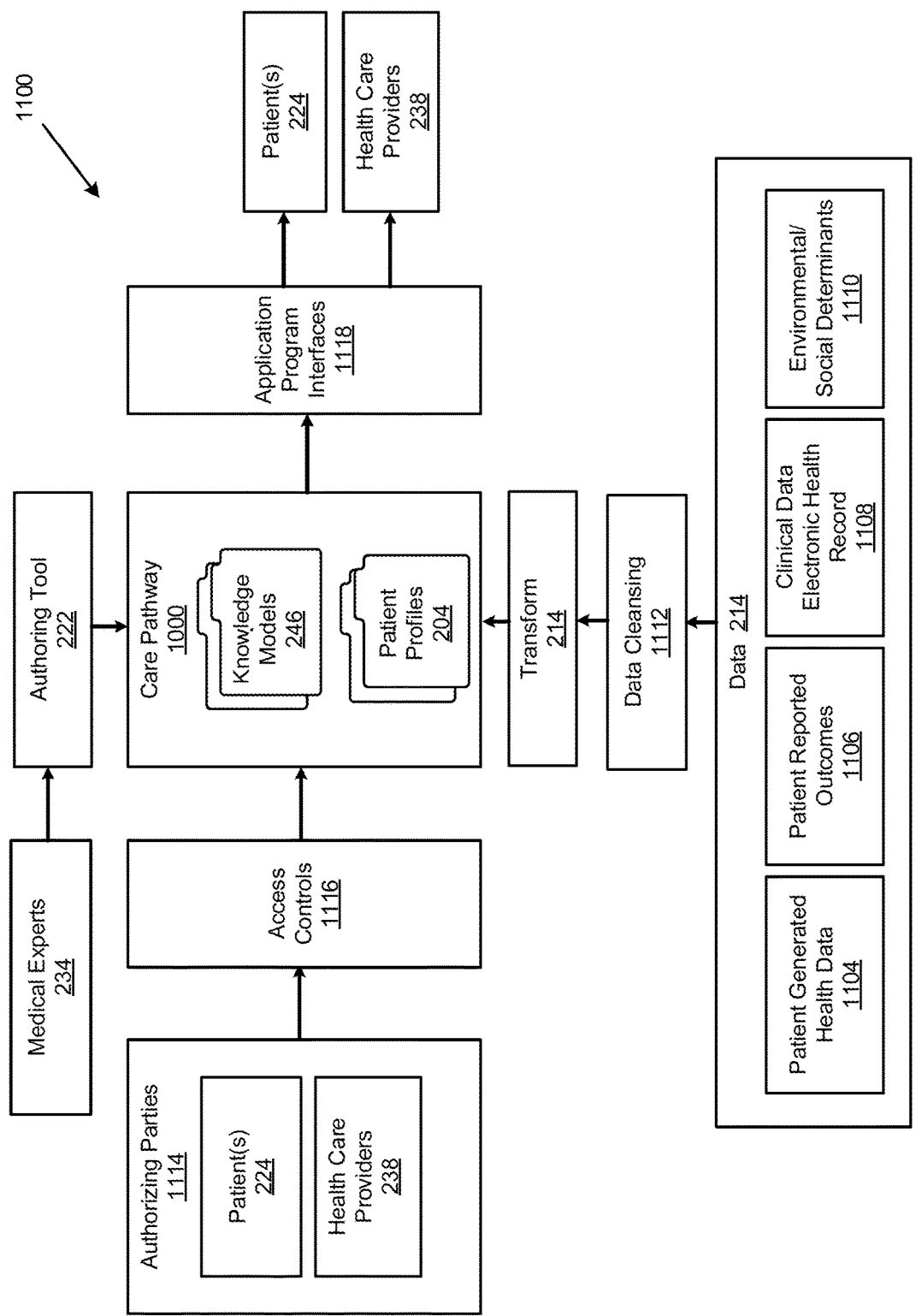
FIGS. 11A-11B show a block diagram of digital therapeutics.

FIG. 11A is a block diagram of digital therapeutics or DTx that can be used to implement the system and method of the present invention.

In certain implementations, the information handling system 100, and the health AI system 118 as described can be used as the platform for DTx 1100. The care pathway 1000 described above, can receive input and provide output by various entities. Included in the care pathway are DTx knowledge models 246 and deep layer patient profiles (DLPP) 204. In certain implementations, medical experts 234, which can include drug and disease experts, provide input as to DTx knowledge models 246 through authoring tool 222.

The care pathway 1000 receives data from data component 1102. Data component 1102 can include patient generated health data 1104, which can include biometrics, etc. Data component 1102 can further include patient reported outcomes data 1106, clinical data (electronic health records) 1108, and environmental/social determinants data 1110. In certain implementations, the data from data component 102 can come from health data 242 and devices 228 described in FIG. 2. In certain implementations, data from data component 102 can be processed by a data cleansing component 1112. Data from data cleansing component can be received by the transform component 214. Data from the transform component 214 can be received by the care pathway 1000.

In certain implementations, authorizing parties 1114 request for treatment, and use of the DTx 1100. Authorizing parties 1114 can include patients 224, which can include actual patients and delegates/caregivers of patients, etc. Authorizing parties 1114 can be health care providers 238, which can include primary prescribing physicians/staff, non-treating physicians/staff, etc.

Entities, such as patients 224 and health care providers 238 can receive output, such as recommendations, from the care pathway 1000. The output from care pathway 1000 can be processed by application program interfaces (API) 1118. In certain implementations, a user interface (UI)/user experience (UX) can be used to provide output (e.g., recommendations) to patients 224 and health care providers 238. In certain implementations, API 1118 can include a localization layer to interface or integrate with different data sources, or cloud environment for deployment.

Figure 11B:
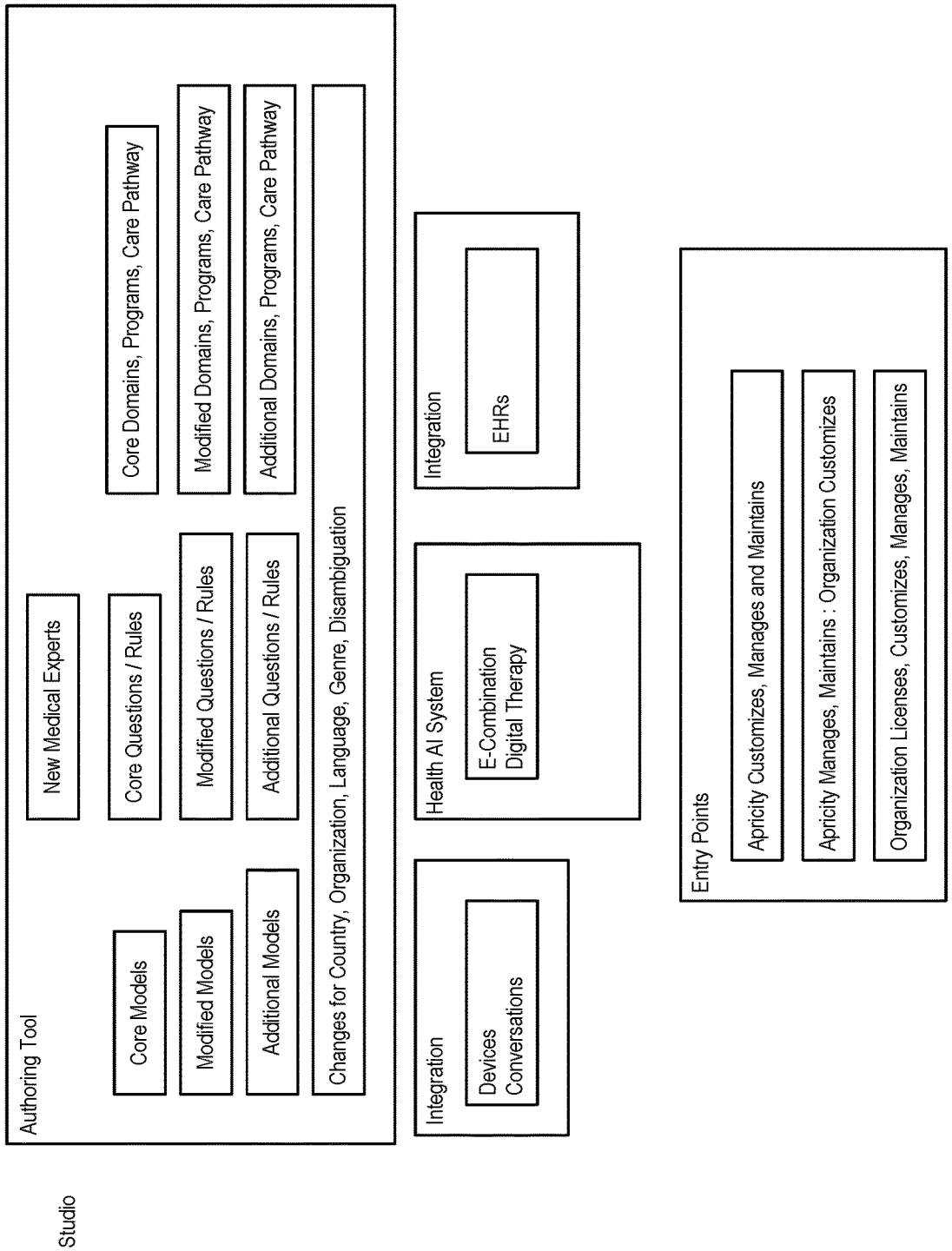

FIG. 11B is a block diagram of another implementation of digital therapeutics or DTx that can be used to implement the system and method of the present invention. Generally, an DTx as a "Studio" can provide permutations of customizable content including domains, programs, rules, actions, conditions, adverse events (see DTX knowledge model above) and care pathways. In additional patients, providers, and experts can be included. The "Studio" can enable multiple deployments of topologies, geographies, and governing laws/regulations, etc. to direct customization and implementation.

The "Studio" can deploy entry points that can include (i) a hosted and managed environment where an organization and its patients use the product without customizations (e.g., clinical trial at existing cancer center with existing patients; (ii) a hosted and managed environment where an organization enhances customizable content; and (iii) an ability for a medical organization and providers to customize and management their own DTx product.

Customizable content can include modified knowledge models, questions, rules, actions, AEs and the method for a care pathway. Studio customization can include the ability to add additional integration of devices, conversation flows and genres. Studio customization can include the ability to add additional integration of EHRs, third party systems and patient data sources. Studio can include selectable and customizable components for modifying care pathway that includes dialog, detect, diagnose and recommend.

Figure 12:
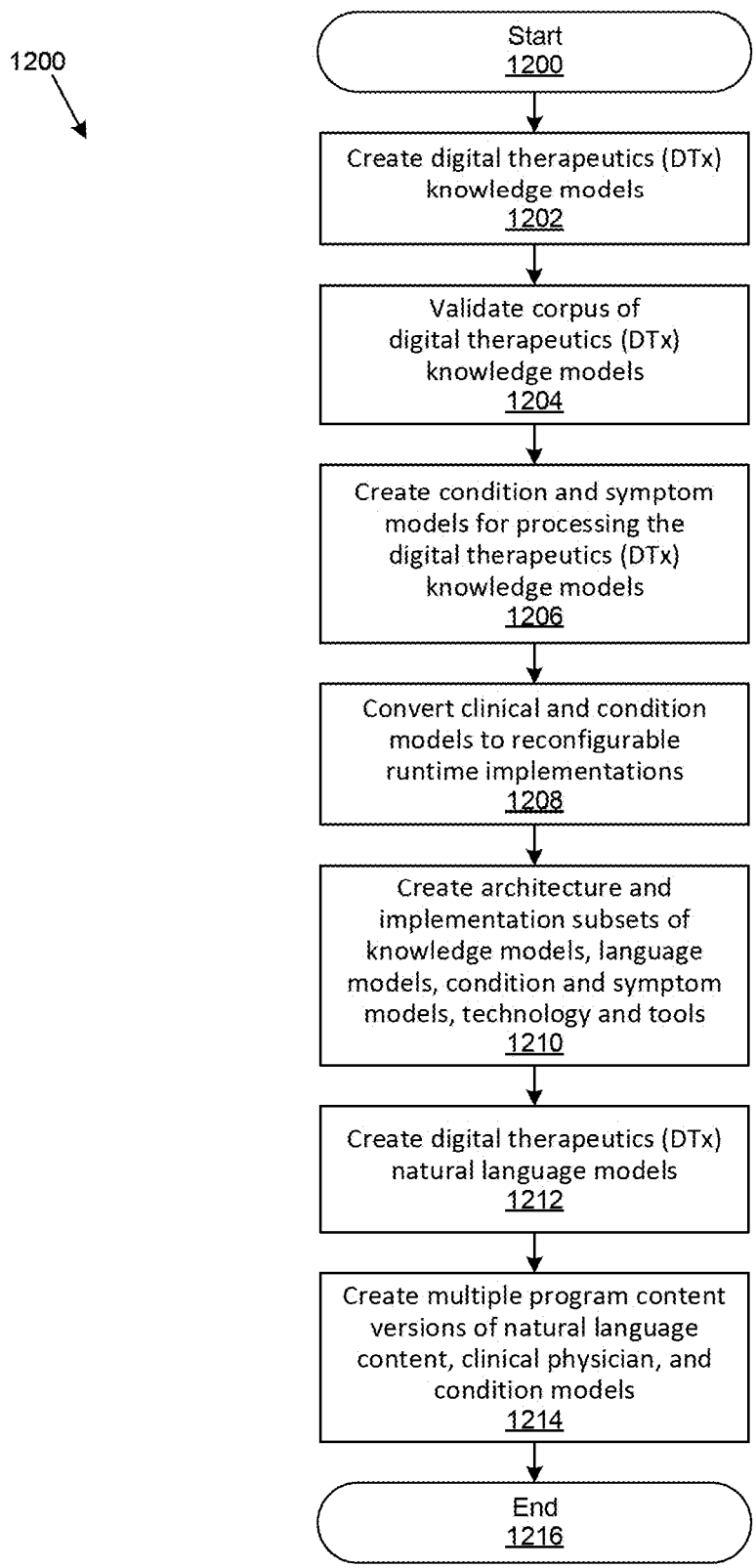
FIG. 12 shows a flowchart for creating digital therapeutics directed to patient care specific to a disease.

FIG. 12 is a generalized flowchart 1200 for creating digital therapeutics directed to patient care specific to a disease. In various embodiments, the health AI system 118 is implemented. In particular, the process 1200 can be performed with components described for example in FIGS. 11A and 11B. The order in which the method is described is not intended to be construed as a limitation, and any number of the described method blocks may be combined in an y order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 1202 the process 1200 starts. At step 1202, creating digital therapeutics (DTx) knowledge models is performed. In particular, the creating is performed using clinical physician expertise. In certain implementations, SME (subject matter expert) clinical expertise, clinical knowledge, published guidelines can be used to create knowledge model representation of toxicity, conditions, symptoms and recommendations. Certain implementations provide for representation to be internally stored as JSON (Javascript object notation). The process 1200 can provide an authoring experience to create and edit each type of model, review, view and test.

At step 1204, validating of corpus of the digital therapeutics (DTx) knowledge models is performed. Clinical experts can review visual results of the knowledge models. The visual representation includes text accuracy, formatting, highlighting and relationships. A set of the knowledge models can be executed to ensure accuracy. Execution can involve running a dialog simulating patient interaction and allows SME to validate results. Testing can test possible allowed combinations and can verified by medical experts. Complete set of testing for out of bounds possibilities can be avoided, considering there can numerous combinations that are not medically relevant.

At step 1206, condition and symptom models are created for processing the digital therapeutics (DTx) knowledge models. Combinations of conditions and symptoms can be created to represent toxicity. A rule-out strategy technique can be implemented, which rules out a condition such as colitis, dermatitis, etc. The rule-out strategy can include time windows, priority, ordering, weight, etc. The goal is not to determine what the toxicity is, but what it is not. The creation of the conditions and symptoms and validation can be provided through the rule-out strategy.

At step 1208, converting of clinical and condition models to reconfigurable runtime implementations is performed, using the digital therapeutics (DTx) knowledge models and digital therapeutics (DTx) natural language models, which can be based on organization, government regulations, treatment protocols, and physician requirements. The process 1200 can enable the creating of technical models that reflect human readable knowledge models. The technical models can be implemented in the artificial intelligence DTx platform. Each organization or governing authority can select which knowledge models, and therefore technical models, they will allow or follow. The DTx platform can allow sets of knowledge models and technical models to be partitioned and implemented.

At step 1210, creating architecture and implementation subsets of knowledge models, language models, condition and symptom models, technology and tools is performed, using the digital therapeutics (DTx) knowledge models and digital therapeutics (DTx) natural language models. Implementation can be for physical and logical deployments based on physician needs, organization constraints, disease outbreaks, emergency care. The DTx platform can be customized by a health care organization or clinical trial. The process 1200 and DTx platform can allow the delivery of a technical package to be executed onsite, in the cloud or remotely managed.

At step 1212, creating digital therapeutics (DTx) natural language models based on the corpus of the digital therapeutics (DTx) knowledge models that generate specific written and spoken languages is performed. The process 1200 can allow for knowledge models to be represented in various natural language models in order to have a dialog with the patient. The natural language can bi-directional, allowing a patient to hear and read questions in a language, and allow for responses in the same or a different language. The canonical natural language for the platform is English. The patient can be presented with one or more natural language. The patient can respond in one or more natural languages. A natural language representation allows for machine learning processing on the dialog to more efficiently process synonyms, ambiguities, genres, slang, pauses, speech engine errors, human speech errors.

At step 1214, creating multiple program content versions of natural language content, clinical physician, and condition models using the digital therapeutics (DTx) knowledge models and digital therapeutics (DTx) natural language models is performed. Through the implementation of process 120 and technical DTx platform, an entire system can be hosted into a new domain of treatment. For example, from cancer immunology to diabetes treatments, to heart disease, etc. Since many diseases may impact or cause other diseases, programs may be combined. For example, cancer treatments can lead to heart disease. In this case, implementations can run and correlate multiple programs of cancer and heart disease.

In certain implementations, creating condition models with weights, time validity periods, extraction of longitudinal patient data, that define patient reported outcomes using the digital therapeutics (DTx) knowledge models and digital therapeutics (DTx) natural language models is further performed.

In certain implementations, creating symptom models for adverse events including but not limited to headaches, bowel movements, blood pressure, rashes, pain threshold, and time periods; plus natural language question, answer text mappings to natural language model numeric intensity for structured and deep layer patient profile (DLPP) storage for representing longitudinal patient reported outcomes is further performed. Traceability can be performed as to the symptom models.

In certain implementations, creating genre specific patient preference-based dialog, conditions, questions and answer ranges for capture, and providing refining of next dialog questions using the digital therapeutics (DTx) knowledge models and digital therapeutics (DTx) natural language models is further performed.

In certain implementations, creating detect toxicity models with trigger, primary and associated symptom mappings that are weighted, prioritized, and time validity using the digital therapeutics (DTx) knowledge models and digital therapeutics (DTx) natural language models is further performed.

In certain implementations, creating diagnose models for diagnosing health condition grades against lab results and patient report systems using the digital therapeutics (DTx) knowledge models and digital therapeutics (DTx) natural language models is further performed.

In certain implementations, creating recommendation models for toxicity treatments to support a digital therapeutics (DTx) care-pathway, clinical guidance, and toxicity avoidance using the digital therapeutics (DTx) knowledge models and digital therapeutics (DTx) natural language models is further performed.

In certain implementations, creating deep layer patient profile (DLPP) images based on structured data, longitudinal data and mappings using the digital therapeutics (DTx) knowledge models and digital therapeutics (DTx) natural language models is further performed.

In certain implementations, creating domain, program and protocol specific implementation deployments for various platform implementations, organization technology and security requirements using the digital therapeutics (DTx) knowledge models and digital therapeutics (DTx) natural language models is performed.

At block 1216, the process 1200 ends.

Referring to FIG. 13, an example screen presentation of a health care provider user interface 1300 is shown. The user interface 1300 provides views into patient reports, status, recommendations, etc.

Figure 14:
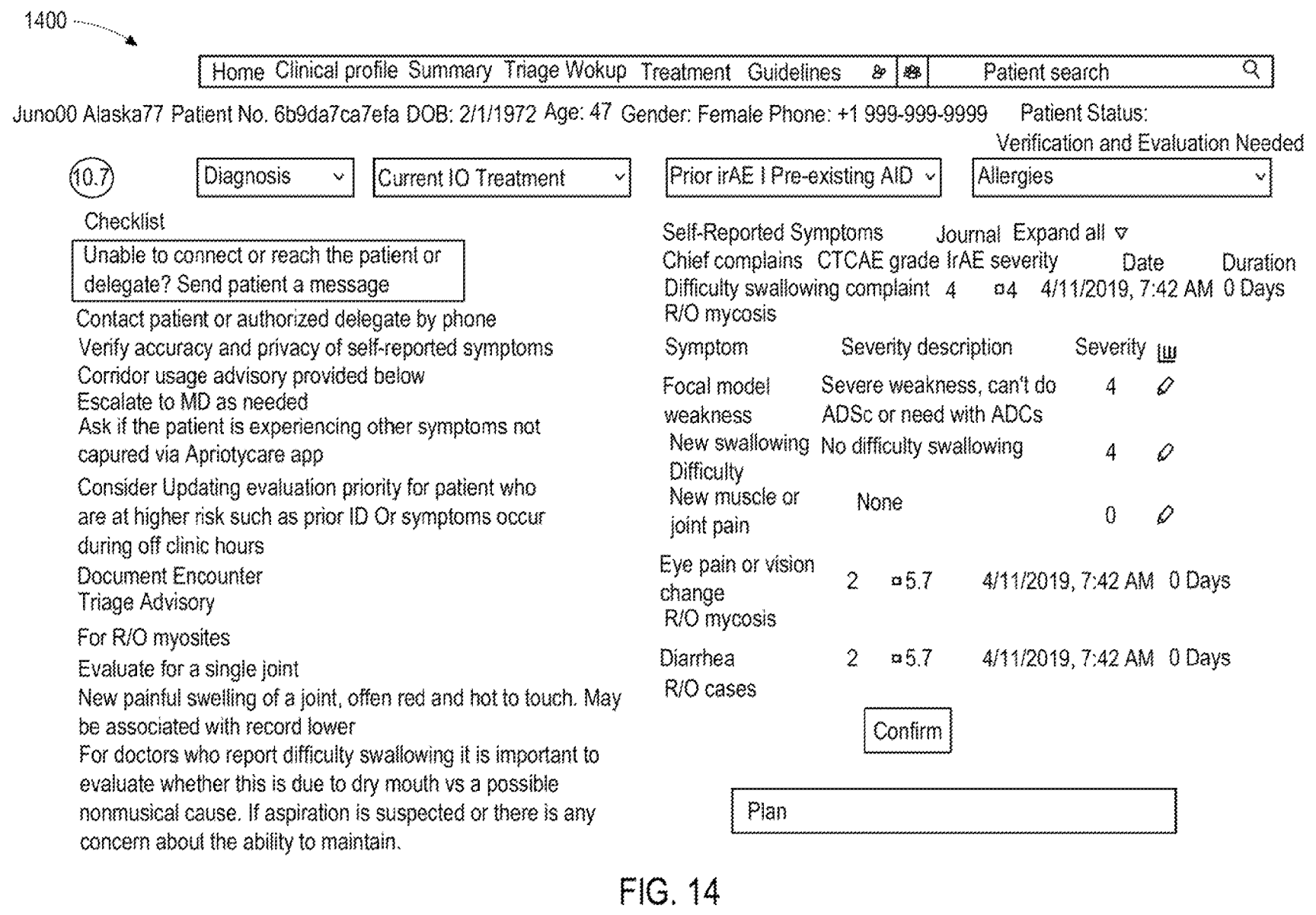

Referring to FIG. 14, an example screen presentation of a health care provider user interface 1400 is shown. The user interface 1400 provides views into patient reports, status, recommendations, etc.

Referring to FIG. 15, an example screen presentation of a health care provider user interface 1500 is shown. The user interface 1500 provides views into patient reports, status, recommendations, etc.

Referring to FIG. 16, an example screen presentation of a health care provider user interface 1600 is shown. The user interface 1600 provides views into patient reports, status, recommendations, etc.

Figure 17:
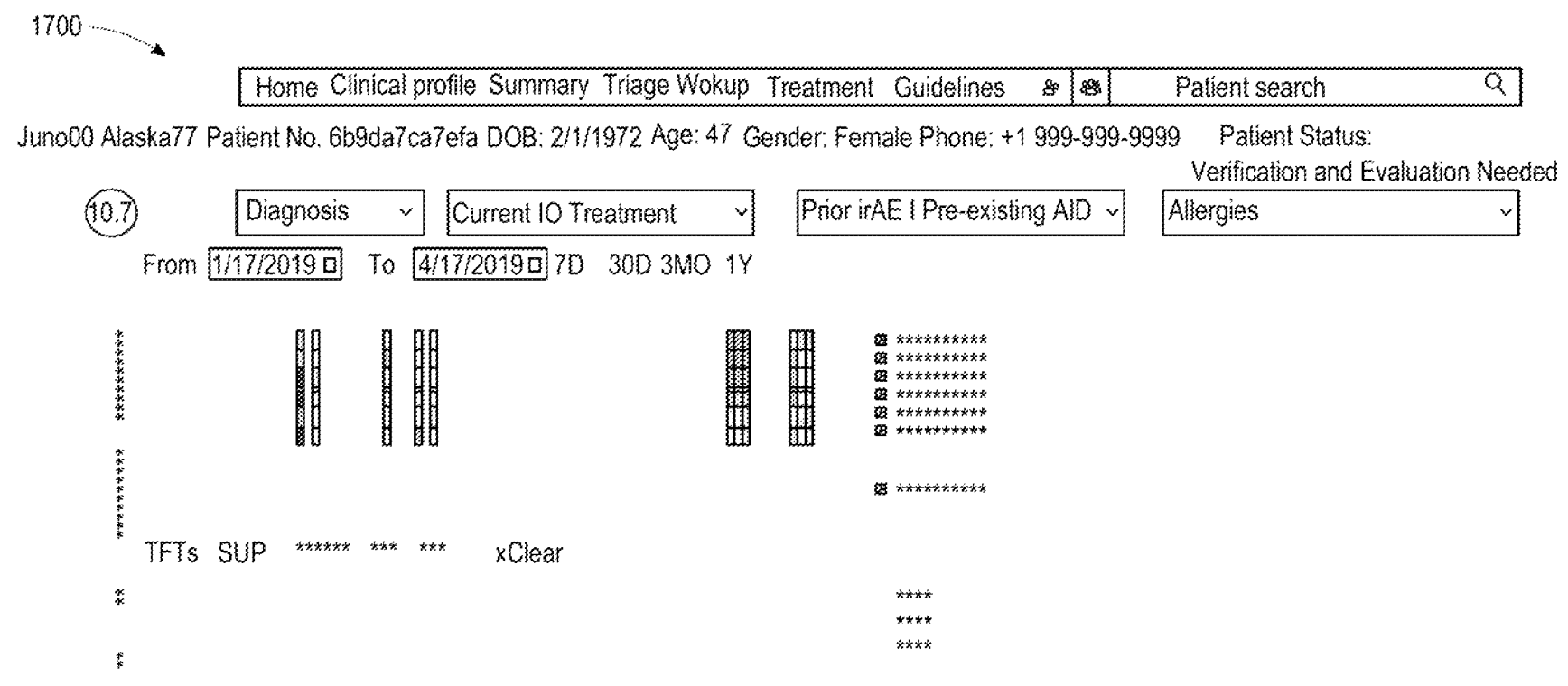

Referring to FIG. 17, an example screen presentation of a health care provider user interface 1700 is shown. The user interface 1700 provides views into patient reports, status, recommendations, etc.

Figure 18:
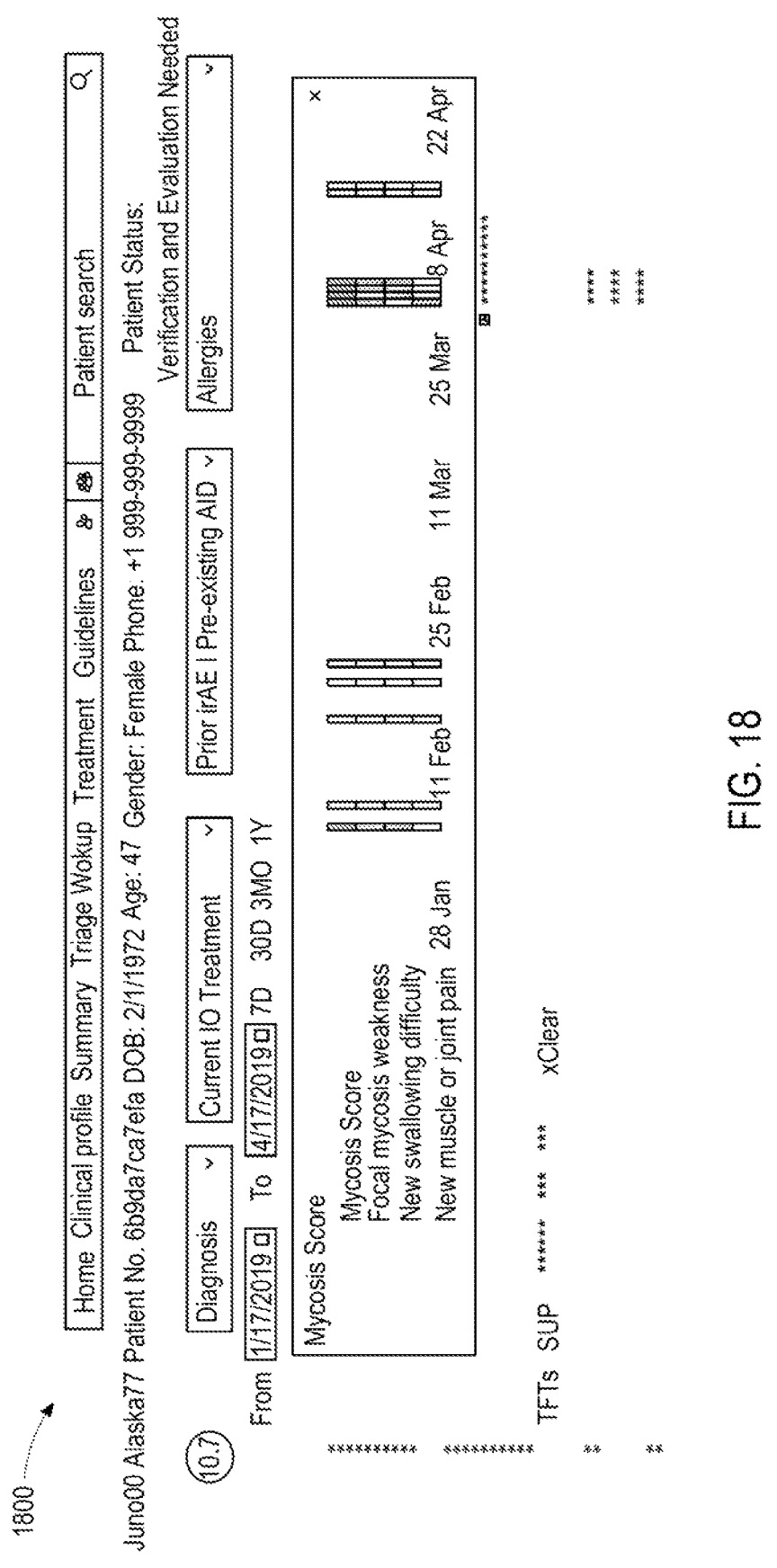

Referring to FIG. 18, an example screen presentation of a health care provider user interface 1800 is shown. The user interface 1800 provides views into patient reports, status, recommendations, etc.

Figures 19, 20:
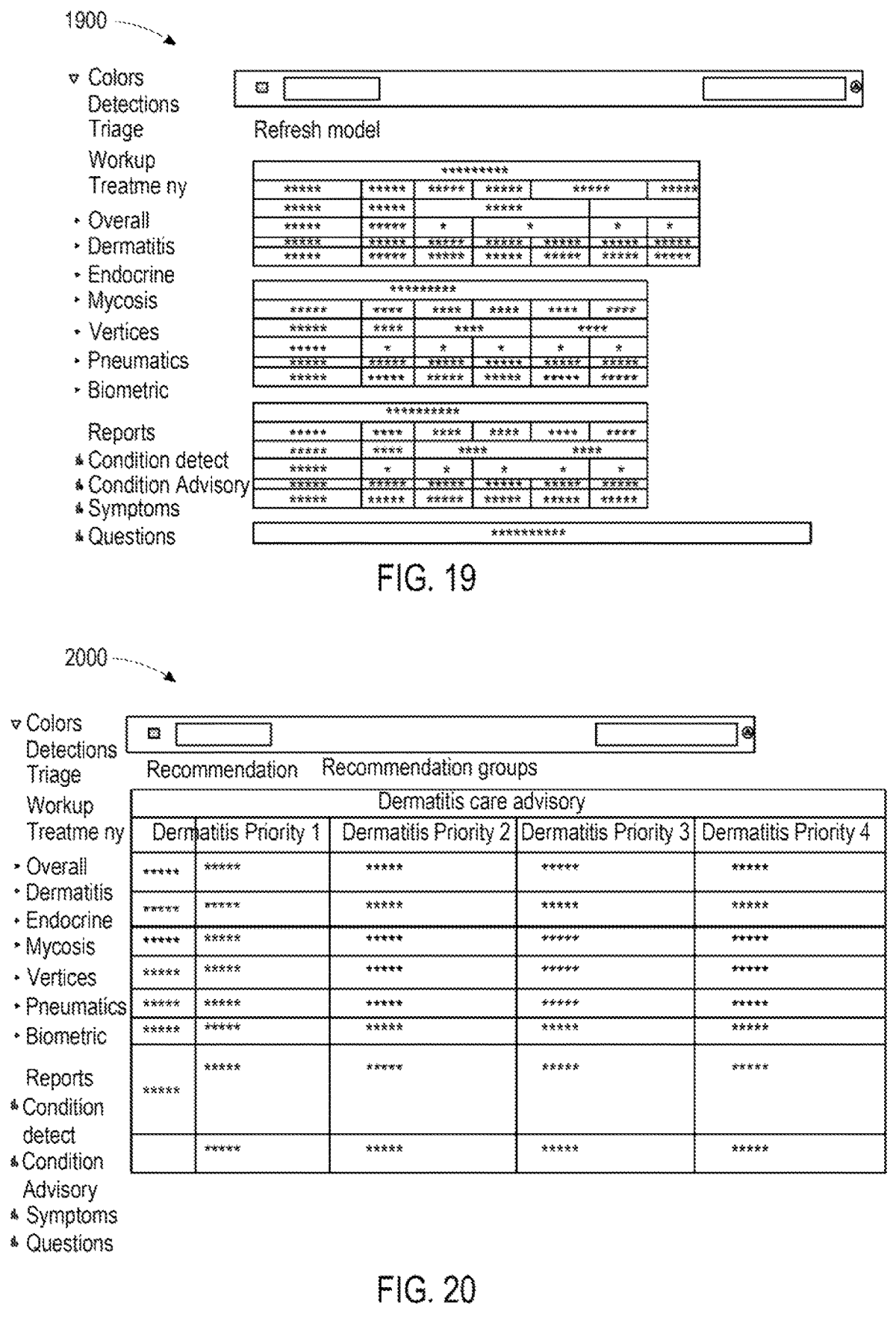

Referring to FIG. 19, an example screen presentation of an authoring tool user interface 1900 is shown. The user interface 1900 provides views as authoring questions, IDs, priorities, conditions, languages, deploy DTx knowledge models, etc.

Referring to FIG. 20, an example screen presentation of an authoring tool user interface 2000 is shown. The user interface 2000 provides views as authoring questions, IDs, priorities, conditions, languages, deploy DTx knowledge models, etc.

Figure 21:
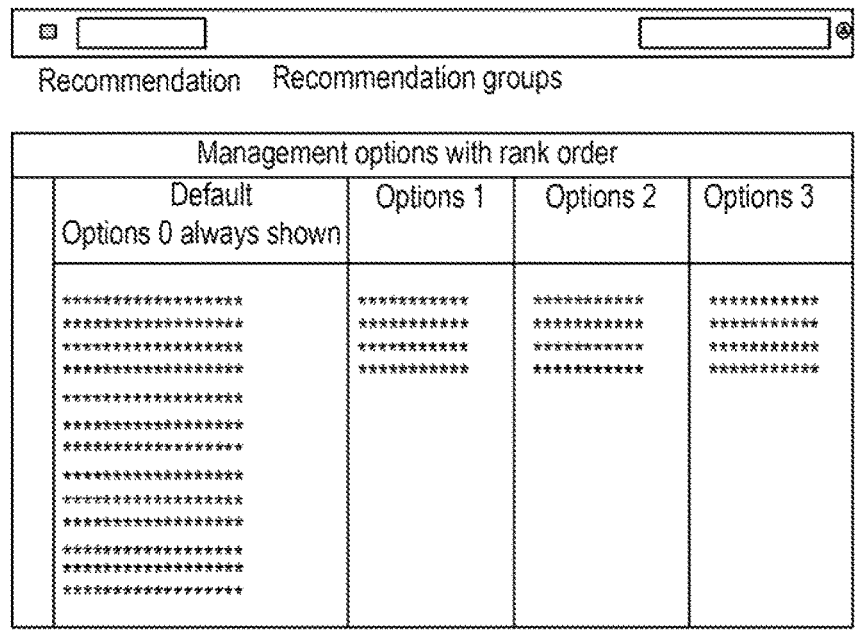
FIG. 21 shows a screen presentation of an authoring tool user interface.

Referring to FIG. 21, an example screen presentation of an authoring tool user interface 2100 is shown. The user interface 2100 provides views as authoring questions, IDs, priorities, conditions, languages, deploy DTx knowledge models, etc.

Figure 22:
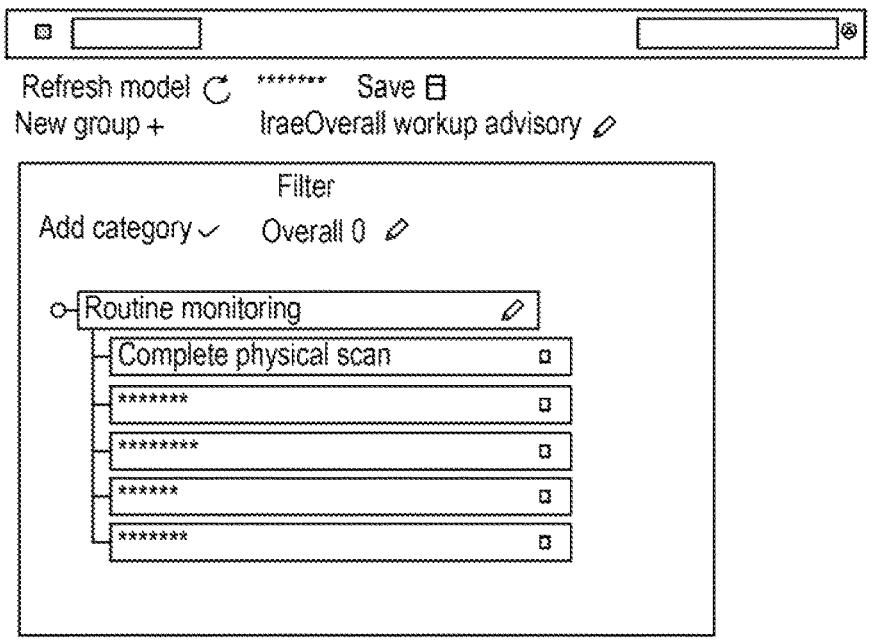
FIG. 22 shows a screen presentation of an authoring tool user interface.

Referring to FIG. 22, an example screen presentation of an authoring tool user interface 2200 is shown. The user interface 2200 provides views as authoring questions, IDs, priorities, conditions, languages, deploy DTx knowledge models, etc.

Figure 23:
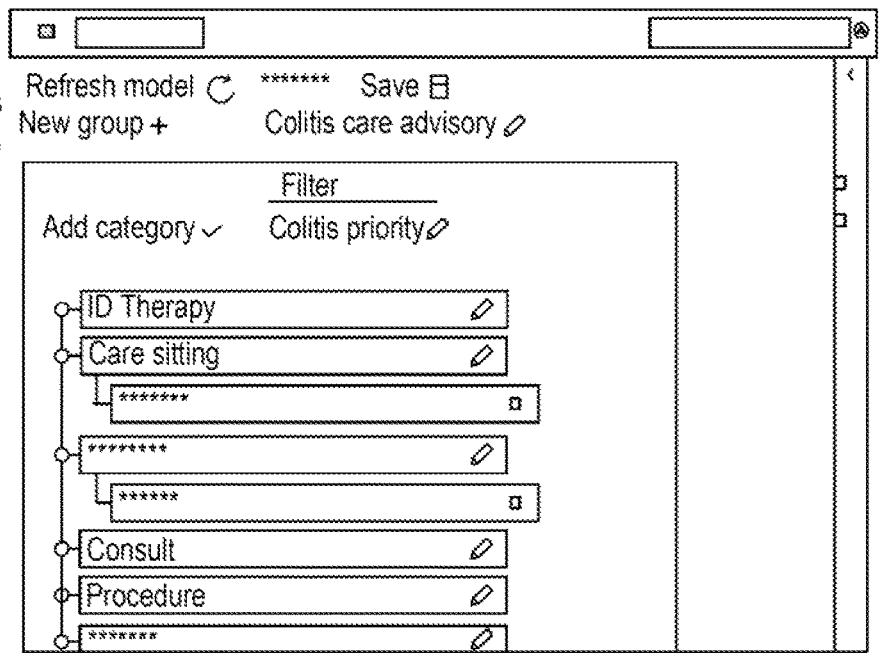
FIG. 23 shows a screen presentation of an authoring tool user interface.

Referring to FIG. 23, an example screen presentation of an authoring tool user interface 2300 is shown. The user interface 2300 provides views as authoring questions, IDs, priorities, conditions, languages, deploy DTx knowledge models, etc.

Figure 24:
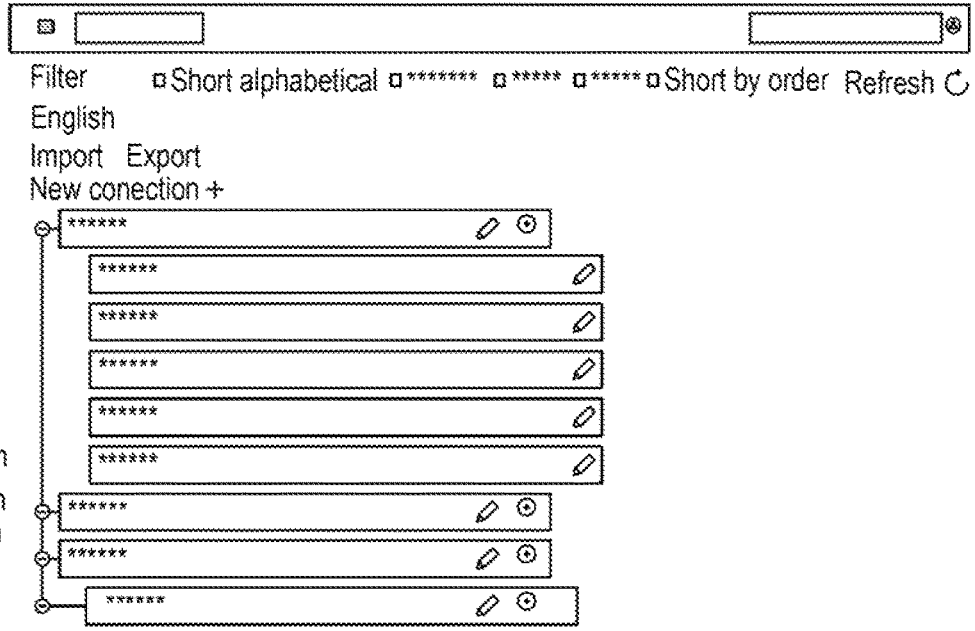
FIG. 24 shows a screen presentation of an authoring tool user interface.

Referring to FIG. 24, an example screen presentation of an authoring tool user interface 2400 is shown. The user interface 2400 provides views as authoring questions, IDs, priorities, conditions, languages, deploy DTx knowledge models, etc.

As will be appreciated by one skilled in the art, the present invention may be embodied as a method, system, or computer program product. Accordingly, embodiments of the invention may be implemented entirely in hardware, entirely in software (including firmware, resident software, microcode, etc.) or in an embodiment combining software and hardware. These various embodiments may all generally be referred to herein as a "component," "circuit," "module," or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, or a magnetic storage device. In the context of this document, a computer-usable or computer-readable medium may be any medium that can contain, store, communicate, or transport the program for use by or in connection with the instruction execution system, apparatus, or device.

Computer program code for carrying out operations of the present invention may be written in a programming language such as JavaScript, Python, C # or the like. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Embodiments of the invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The present invention is well adapted to attain the advantages mentioned as well as others inherent therein. While the present invention has been depicted, described, and is defined by reference to particular embodiments of the invention, such references do not imply a limitation on the invention, and no such limitation is to be inferred. The invention is capable of considerable modification, alteration, and equivalents in form and function, as will occur to those ordinarily skilled in the pertinent arts. The depicted and described embodiments are examples only and are not exhaustive of the scope of the invention.

Consequently, the invention is intended to be limited only by the spirit and scope of the appended claims, giving full cognizance to equivalents in all respects.

What is claimed is:

1. A computer-implementable method of processing patient related information in a health artificial intelligence system comprising:
    creating digital therapeutics (DTx) knowledge models from clinical physician expertise;
    validating corpus of the digital therapeutics (DTx) knowledge models that generate specific written and spoken languages;
    creating condition models and symptom models for processing the digital therapeutics (DTx) knowledge models;
    creating digital therapeutics (DTx) natural language models based on the corpus of the digital therapeutics (DTx) knowledge models that generate specific written and spoken languages;
    converting clinical models and the condition models to reconfigurable runtime implementations based on organization, government regulations, treatment protocols, and physician requirements using the digital therapeutics (DTx) knowledge models and digital therapeutics (DTx) natural language models;
    creating multiple program content versions of natural language content, clinical physician, and the converted condition models using the digital therapeutics (DTx) knowledge models and digital therapeutics (DTx) natural language models; and
    creating deep layer patient profiles (DLPP) of patient data used to turn related and structured patient data into a multidimensional unstructured data format that is processed with machine learning and image processing algorithms, wherein the DLPP is anonymized to be implemented with algorithms focused on binary and intensity operations that include image processing and image learning.

2. The computer-implementable method of claim 1 wherein the creating condition models further comprises the use of weights, time validity periods, extraction of longitudinal patient data, that define patient reported outcomes using the digital therapeutics (DTx) knowledge models and digital therapeutics (DTx) natural language models.

3. The computer-implementable method of claim 1 further comprising creating symptom models for adverse events including headaches, bowel movements, blood pressure, rashes, pain threshold, and time periods; plus natural language question, answer text mappings to natural language model numeric intensity for structured and deep layer patient profile (DLPP) storage for representing longitudinal patient reported outcomes.

4. The computer-implementable method of claim 3 further comprising providing traceability to the symptom models.

5. The computer-implementable method of claim 1 further comprising creating genre specific patient preference-based dialog, conditions, questions and answer ranges for capture, and providing refining of next dialog questions using the digital therapeutics (DTx) knowledge models and digital therapeutics (DTx) natural language models.

6. The computer-implementable method of claim 1 further comprising creating detect toxicity models with trigger, primary and associated symptom mappings that are weighted, prioritized, and time validity using the digital therapeutics (DTx) knowledge models and digital therapeutics (DTx) natural language models.

7. The computer-implementable method of claim 1 further comprising creating diagnose models for diagnosing health condition grades against lab results and patient report systems using the digital therapeutics (DTx) knowledge models and digital therapeutics (DTx) natural language models.

8. The computer-implementable method of claim 1 further comprising creating recommendation models for toxicity treatments to support a digital therapeutics (DTx) care-pathway, clinical guidance, and toxicity avoidance using the digital therapeutics (DTx) knowledge models and digital therapeutics (DTx) natural language models.

9. The computer-implementable method of claim 1 further comprising creating deep layer patient profile (DLPP) images based on the structured patient data, longitudinal data and mappings using the digital therapeutics (DTx) knowledge models and digital therapeutics (DTx) natural language models.

10. The computer-implementable method of claim 1 further comprising creating domain, program and protocol specific implementation deployments for various platform implementations, organization technology and security requirements using the digital therapeutics (DTx) knowledge models and digital therapeutics (DTx) natural language models.

11. A system comprising:
a processor;
a data bus coupled to the processor; and;
a non-transitory, computer-readable storage medium embodying computer program code, the non-transitory, computer-readable storage medium being coupled to the data bus, the computer program code interacting with a plurality of computer operations and comprising instructions executable by the processor and configured for:
creating digital therapeutics (DTx) knowledge models from clinical physician expertise;
validating corpus of the digital therapeutics (DTx) knowledge models that generate specific written and spoken languages;
creating condition models and symptom models for processing the digital therapeutics (DTx) knowledge models;
creating digital therapeutics (DTx) natural language models based on the corpus of the digital therapeutics (DTx) knowledge models that generate specific written and spoken languages;
converting clinical models and the condition models to reconfigurable runtime implementations based on organization, government regulations, treatment protocols, and physician requirements using the digital therapeutics (DTx) knowledge models and digital therapeutics (DTx) natural language models;
creating multiple program content versions of natural language content, clinical physician, and the converted condition models using the digital therapeutics (DTx) knowledge models and digital therapeutics (DTx) natural language models; and
creating deep layer patient profiles (DLPP) of patient data used to turn related and structured patient data into a multidimensional unstructured data format that is processed with machine learning and image processing algorithms, wherein the DLPP is anonymized to be implemented with algorithms focused on binary and intensity operations that include image processing and image learning.

12. The system of claim 11 wherein the creating condition models further comprises the use of weights, time validity periods, extraction of longitudinal patient data, that define patient reported outcomes using the digital therapeutics (DTx) knowledge models and digital therapeutics (DTx) natural language models.

13. The system of claim 11 further comprising creating symptom models for adverse events including headaches, bowel movements, blood pressure, rashes, pain threshold, and time periods; plus natural language question, answer text mappings to natural language model numeric intensity for structured and deep layer patient profile (DLPP) storage for representing longitudinal patient reported outcomes.

14. The system of claim 13 further comprising providing traceability to the symptom models.

15. The system of claim 11 further comprising creating genre specific patient preference-based dialog, conditions, questions and answer ranges for capture, and providing refining of next dialog questions using the digital therapeutics (DTx) knowledge models and digital therapeutics (DTx) natural language models.

16. The system of claim 11 further comprising creating detect toxicity models with trigger, primary and associated symptom mappings that are weighted, prioritized, and time validity using the digital therapeutics (DTx) knowledge models and digital therapeutics (DTx) natural language models.

17. The system of claim 11 further comprising creating diagnose models for diagnosing health condition grades against lab results and patient report systems using the digital therapeutics (DTx) knowledge models and digital therapeutics (DTx) natural language models.

18. The system of claim 11 further comprising creating recommendation models for toxicity treatments to support a digital therapeutics (DTx) care-pathway, clinical guidance, and toxicity avoidance using the digital therapeutics (DTx) knowledge models and digital therapeutics (DTx) natural language models.

19. The system of claim 11 further comprising creating deep layer patient profile (DLPP) images based on the structured patient data, longitudinal data and mappings using the digital therapeutics (DTx) knowledge models and digital therapeutics (DTx) natural language models.

20. The system of claim 11 further comprising creating domain, program and protocol specific implementation deployments for various platform implementations, organization technology and security requirements using the digital therapeutics (DTx) knowledge models and digital therapeutics (DTx) natural language models.

21. A non-transitory, computer-readable storage medium embodying computer program code, the computer program code comprising computer executable instructions configured for:
creating digital therapeutics (DTx) knowledge models from clinical physician expertise;
validating corpus of the digital therapeutics (DTx) knowledge models that generate specific written and spoken languages;
creating condition models and symptom models for processing the digital therapeutics (DTx) knowledge models;

creating digital therapeutics (DTx) natural language models based on the corpus of the digital therapeutics (DTx) knowledge models that generate specific written and spoken languages;
converting clinical models and the condition models to reconfigurable runtime implementations based on organization, government regulations, treatment protocols, and physician requirements using the digital therapeutics (DTx) knowledge models and digital therapeutics (DTx) natural language models;
creating multiple program content versions of natural language content, clinical physician, and the converted condition models using the digital therapeutics (DTx) knowledge models and digital therapeutics (DTx) natural language models; and
creating deep layer patient profiles (DLPP) of patient data used to turn related and structured patient data into a multidimensional unstructured data format that is processed with machine learning and image processing algorithms, wherein the DLPP is anonymized to be implemented with algorithms focused on binary and intensity operations that include image processing and image learning.

22. The non-transitory, computer-readable storage medium of claim 21 wherein the creating condition models further comprises the use of weights, time validity periods, extraction of longitudinal patient data, that define patient reported outcomes using the digital therapeutics (DTx) knowledge models and digital therapeutics (DTx) natural language models.

23. The non-transitory, computer-readable storage medium of claim 21 further comprising creating symptom models for adverse events including headaches, bowel movements, blood pressure, rashes, pain threshold, and time periods; plus natural language question, answer text mappings to natural language model numeric intensity for structured and deep layer patient profile (DLPP) storage for representing longitudinal patient reported outcomes.

24. The non-transitory, computer-readable storage medium of claim 23 further comprising providing traceability to the symptom models.

25. The non-transitory, computer-readable storage medium of claim 21 further comprising creating genre specific patient preference-based dialog, conditions, questions and answer ranges for capture, and providing refining of next dialog questions using the digital therapeutics (DTx) knowledge models and digital therapeutics (DTx) natural language models.

26. The non-transitory, computer-readable storage medium of claim 21 further comprising creating detect toxicity models with trigger, primary and associated symptom mappings that are weighted, prioritized, and time validity using the digital therapeutics (DTx) knowledge models and digital therapeutics (DTx) natural language models.

27. The non-transitory, computer-readable storage medium of claim 21 further comprising creating diagnose models for diagnosing health condition grades against lab results and patient report systems using the digital therapeutics (DTx) knowledge models and digital therapeutics (DTx) natural language models.

28. The non-transitory, computer-readable storage medium of claim 21 further comprising creating recommendation models for toxicity treatments to support a digital therapeutics (DTx) care-pathway, clinical guidance, and toxicity avoidance using the digital therapeutics (DTx) knowledge models and digital therapeutics (DTx) natural language models.

29. The non-transitory, computer-readable storage medium of claim 21 further comprising creating deep layer patient profile (DLPP) images based on the structured patient data, longitudinal data and mappings using the digital therapeutics (DTx) knowledge models and digital therapeutics (DTx) natural language models.

30. The non-transitory, computer-readable storage medium of claim 21 further comprising creating domain, program and protocol specific implementation deployments for various platform implementations, organization technology and security requirements using the digital therapeutics (DTx) knowledge models and digital therapeutics (DTx) natural language models.

* * * * *